(12) United States Patent
Park et al.

(10) Patent No.: US 11,798,204 B2
(45) Date of Patent: Oct. 24, 2023

(54) SYSTEMS AND METHODS OF IMAGE PROCESSING BASED ON GAZE DETECTION

(71) Applicant: QUALCOMM Incorporated, San Diego, CA (US)

(72) Inventors: Hyunsin Park, Gwangmyeong (KR); Juntae Lee, Seoul (KR); Simyung Chang, Suwon (KR); Byeonggeun Kim, Seoul (KR); Jaewon Choi, Seoul (KR); Kyu Woong Hwang, Daejeon (KR)

(73) Assignee: QUALCOMM Incorporated, San Diego, CA (US)

( * ) Notice: Subject to any disclaimer, the term of this patent is extended or adjusted under 35 U.S.C. 154(b) by 36 days.

(21) Appl. No.: 17/685,278

(22) Filed: Mar. 2, 2022

(65) Prior Publication Data
US 2023/0281885 A1      Sep. 7, 2023

(51) Int. Cl.
*G06T 11/00*      (2006.01)
*G06V 40/16*      (2022.01)
(Continued)

(52) U.S. Cl.
CPC .............. *G06T 11/00* (2013.01); *G06F 3/013* (2013.01); *G06V 40/174* (2022.01); *G06V 40/18* (2022.01)

(58) Field of Classification Search
CPC ....... G06T 11/00; G06F 3/013; G06V 40/174; G06V 40/18
See application file for complete search history.

(56) References Cited

U.S. PATENT DOCUMENTS 5,675,376 A * 10/1997 Andersson ............. H04N 7/142
 348/E7.079
6,496,217 B1 * 12/2002 Piotrowski ............. H04N 19/89
 375/E7.005
(Continued)

FOREIGN PATENT DOCUMENTS

| EP | 3461125 A1 | 3/2019 |
| EP | 4113982 A1 | 1/2023 |
| WO | 2022260797 A1 | 12/2022 |

OTHER PUBLICATIONS

International Search Report and Written Opinion—PCT/US2023/013237—ISA/EPO—May 24, 2023.
(Continued)

*Primary Examiner* — Benyam Ketema
(74) *Attorney, Agent, or Firm* — QUALCOMM Incorporated

(57) ABSTRACT

Imaging systems and techniques are described. An imaging system receives image data representing at least a portion (e.g., a face) of a first user as captured by a first image sensor. The imaging system identifies that a gaze of the first user as represented in the image data is directed toward a displayed representation of at least a portion (e.g., a face) of a second user. The imaging system identifies an arrangement of representations of users for output. The imaging system generates modified image data based on the gaze and the arrangement at least in part by modifying the image data to modify at least the portion of the first user in the image data to be visually directed toward a direction corresponding to the second user based on the gaze and the arrangement. The imaging system outputs the modified image data arranged according to the arrangement.

30 Claims, 8 Drawing Sheets

(51) Int. Cl.
*G06F 3/01* (2006.01)
*G06V 40/18* (2022.01)

(56) References Cited

U.S. PATENT DOCUMENTS

| | | | | |
|---|---|---|---|---|
| 6,507,356 | B1* | 1/2003 | Jackel | H04N 7/142 |
| | | | | 348/14.06 |
| 6,744,927 | B1* | 6/2004 | Kato | G11B 20/18 |
| 6,753,900 | B2* | 6/2004 | Runcie | H04N 7/144 |
| | | | | 348/E7.083 |
| 7,460,150 | B1* | 12/2008 | Coughlan | H04N 7/15 |
| | | | | 348/333.03 |
| 7,605,837 | B2* | 10/2009 | Yuen | H04N 7/144 |
| | | | | 348/14.07 |
| 9,424,678 | B1* | 8/2016 | Enakiev | G01B 11/24 |
| 9,485,459 | B2* | 11/2016 | Shoemake | H04N 7/141 |
| 9,521,325 | B2* | 12/2016 | Yu | H04N 23/68 |
| 9,596,401 | B2* | 3/2017 | Thorn | H04M 1/0264 |
| 9,678,567 | B2* | 6/2017 | Buford | G06F 3/013 |
| 9,820,004 | B1* | 11/2017 | Foerster | H04N 21/8126 |
| 9,832,372 | B1* | 11/2017 | Conway, Sr. | H04L 65/403 |
| 9,942,518 | B1* | 4/2018 | Tangeland | G06V 10/763 |
| 10,048,749 | B2* | 8/2018 | Miao | H04N 23/611 |
| 10,148,913 | B2* | 12/2018 | Nimri | G10L 21/0272 |
| 10,187,579 | B1* | 1/2019 | Wang | H04N 7/147 |
| 10,257,465 | B2* | 4/2019 | Tangeland | G06F 18/23 |
| 10,359,842 | B2* | 7/2019 | Mizuhara | A61B 3/113 |
| 10,582,117 | B1* | 3/2020 | Tanaka | G06F 3/013 |
| 11,182,619 | B2* | 11/2021 | Cavenaugh | G06V 20/46 |
| 11,418,760 | B1* | 8/2022 | Lanier | G06F 3/013 |
| 11,477,393 | B2* | 10/2022 | Bryan | G06T 7/70 |
| 2010/0208078 | A1* | 8/2010 | Tian | G06T 7/73 |
| | | | | 348/169 |
| 2010/0220897 | A1 | 9/2010 | Ueno et al. | |
| 2012/0092436 | A1* | 4/2012 | Pahud | G06F 3/017 |
| | | | | 348/14.02 |
| 2012/0293606 | A1* | 11/2012 | Watson | H04N 23/60 |
| | | | | 348/E7.085 |
| 2015/0215351 | A1* | 7/2015 | Barzuza | H04N 7/157 |
| | | | | 715/757 |
| 2015/0288923 | A1* | 10/2015 | Kim | H04N 23/62 |
| | | | | 348/14.05 |
| 2016/0165130 | A1* | 6/2016 | Cleveland | G06F 3/0325 |
| | | | | 348/47 |
| 2016/0210432 | A1* | 7/2016 | Mizuhara | G16H 80/00 |
| 2016/0234461 | A1* | 8/2016 | Mizuhara | H04N 7/147 |
| 2016/0234475 | A1* | 8/2016 | Courchesne | H04N 7/157 |
| 2016/0316170 | A1* | 10/2016 | Smith | H04N 13/257 |
| 2016/0370975 | A1* | 12/2016 | Collins | G06F 3/04817 |
| 2017/0206691 | A1* | 7/2017 | Harrises | G02B 27/0172 |
| 2017/0339372 | A1* | 11/2017 | Valli | G06T 15/005 |
| 2021/0360195 | A1 | 11/2021 | Oz et al. | |
| 2022/0214743 | A1* | 7/2022 | Dascola | G06F 3/011 |
| 2022/0253136 | A1* | 8/2022 | Holder | G06F 3/013 |
| 2022/0334635 | A1* | 10/2022 | Hawkins | H04N 7/147 |
| 2023/0147584 | A1* | 5/2023 | Asgekar | G06V 40/10 |
| | | | | 382/103 |

OTHER PUBLICATIONS

Narayanan R., et al., "Multiparty Gaze Preservation Through Perspective Switching for Interactive E learning Environments", Multimedia Tools and Applications, Kluwer Academic Publishers, Boston, US, vol. 78, No. 13, Jan. 8, 2019, pp. 17461-17494, XP036832512, ISSN: 1380-7501, DOI: 10.1007/S11042-018-7078-Y, The whole document.

Zhenyi H., et al., "LookAtChat: Visualizing Gaze Awareness for Remote Small-Group Conversations", arxiv.org, Cornell University Library, 201 Olin Library Cornell University Ithaca, NY 14853, Aug. 5, 2021, 23 Pages, XP091026044, The whole document.

* cited by examiner

SYSTEMS AND METHODS OF IMAGE PROCESSING BASED ON GAZE DETECTION

FIELD

This application is related to image processing based on gaze detection. More specifically, this application relates to systems and methods of detecting that a gaze of a first user is on a representation of a second user, and modifying a representation of at least a portion of the first user to be indicative of the gaze of the first user being on the second user, for instance by changing eye pose, head pose, and/or body pose so that at least a portion of the first user appears to be turned toward or otherwise directed toward the second user and/or a representation of the second user.

BACKGROUND

Video conferencing is a network-based technology that allows multiple users, who may each be in different locations, to connect in a video conference over a network using respective user devices that generally each include displays and cameras. In video conferencing, each camera of each user device captures image data representing the corresponding user and sends that image data to the other user devices connected to the video conference to be displayed to the other users using the displays of the other user devices. Meanwhile, the user device displays image data representing the other users in the video conference, captured by the respective cameras of the other user devices that those other users use to connect to the video conference. Video conferencing can be used by a group of users to virtually speak face-to-face while users are in different locations. Video conferencing can be a valuable way to users to virtually meet with each other despite travel restrictions, such as those related to a pandemic.

At a true in-person meeting, it is generally visible who is looking where (e.g., at who) at a given moment, which can provide important context. On the other hand, a user in a video conference generally cannot see where (e.g., at who) other users in the video conference are looking. For instance, depictions of the same user may be arranged in different ways by the different user devices attending the video conference, so even if it is visible that a given user is looking at a specific portion of their screen, it can still be unclear who the user is looking at.

BRIEF SUMMARY

In some examples, systems and techniques are described for image processing. An imaging system receives image data representing at least a portion (e.g., a face) of a first user as captured by a first image sensor. The imaging system identifies that a gaze of the first user as represented in the image data is directed toward a displayed representation of at least a portion (e.g., a face) of a second user. For instance, the imaging system can determine that the gaze of the first user is on an upper-right corner of a display screen of the first user's device while the upper-right corner of the display screen of the first user's device is displaying an image of a second user—and therefore that the gaze of the first user is on the second user. The imaging system identifies an arrangement of representations of users for output. For instance, the arrangement may include a grid of the representations of users, where each cell of the grid includes a different user's representation. The imaging system generates modified image data based on the gaze and the arrangement at least in part by modifying the image data to modify at least the portion of the first user in the image data to be visually directed toward a direction corresponding to the second user based on the gaze and the arrangement. For instance, the imaging system can use one or more trained machine learning models to generate the modified image data based on the gaze and the arrangement. For instance, if the second user is viewing the display, then in the modified image data, the first user can be directed toward the position of the second user while the second user views the display. If a third user is viewing the display, and the arrangement includes a representation of the second user then in the modified image data, the first user can be directed toward the position of the representation of the second user in the arrangement. The imaging system outputs the modified image data arranged according to the arrangement, for instance by displaying the modified image data and/or sending the modified image data to a recipient device.

In one example, an apparatus for media processing is provided. The apparatus includes a memory and one or more processors (e.g., implemented in circuitry) coupled to the memory. The one or more processors are configured to and can: receive image data representing at least a portion of a first user as captured by a first image sensor; identify that a gaze of the first user as represented in the image data is directed toward a displayed representation of at least a portion of a second user; identify an arrangement of representations of users for output; generate modified image data based on the gaze and the arrangement at least in part by modifying the image data to modify at least the portion of the first user in the image data to be visually directed toward a direction corresponding to the second user based on the gaze and the arrangement; and output the modified image data arranged according to the arrangement.

In another example, a method of image processing is provided. The method includes: receiving image data representing at least a portion of a first user as captured by a first image sensor; identifying that a gaze of the first user as represented in the image data is directed toward a displayed representation of at least a portion of a second user; identifying an arrangement of representations of users for output; generating modified image data based on the gaze and the arrangement at least in part by modifying the image data to modify at least the portion of the first user in the image data to be visually directed toward a direction corresponding to the second user based on the gaze and the arrangement; and outputting the modified image data arranged according to the arrangement.

In another example, a non-transitory computer-readable medium is provided that has stored thereon instructions that, when executed by one or more processors, cause the one or more processors to: receive image data representing at least a portion of a first user as captured by a first image sensor; identify that a gaze of the first user as represented in the image data is directed toward a displayed representation of at least a portion of a second user; identify an arrangement of representations of users for output; generate modified image data based on the gaze and the arrangement at least in part by modifying the image data to modify at least the portion of the first user in the image data to be visually directed toward a direction corresponding to the second user based on the gaze and the arrangement; and output the modified image data arranged according to the arrangement.

In another example, an apparatus for image processing is provided. The apparatus includes: means for receiving image data representing at least a portion of a first user as captured by a first image sensor; means for identifying that a gaze of the first user as represented in the image data is directed toward a displayed representation of at least a portion of a second user; means for identifying an arrangement of representations of users for output; means for generating modified image data based on the gaze and the arrangement at least in part by modifying the image data to modify at least the portion of the first user in the image data to be visually directed toward a direction corresponding to the second user based on the gaze and the arrangement; and means for outputting the modified image data arranged according to the arrangement.

In some aspects, modifying at least the portion of the first user in the image data to be visually directed toward the direction corresponding to the second user includes modifying an eye pose of at least one eye of the first user in the image data to be visually directed toward the direction corresponding to the second user. In some aspects, modifying at least the portion of the first user in the image data to be visually directed toward the direction corresponding to the second user includes modifying a head pose of at least part of a head of the first user in the image data to be visually directed toward the direction corresponding to the second user. In some aspects, modifying at least the portion of the first user in the image data to be visually directed toward the direction corresponding to the second user includes modifying a body pose of at least part of a body of the first user in the image data to be visually directed toward the direction corresponding to the second user.

In some aspects, the arrangement of representations of users includes the modified image data and second image data representing at least the portion of the second user, wherein the direction corresponding to the second user is a direction from a position of the modified image data in the arrangement to a position of the second image data in the arrangement, wherein at least a component of the direction corresponding to the second user is parallel to an image plane of the arrangement. In some aspects, the second user is a viewer of the modified image data as output according to the arrangement, wherein the direction corresponding to the second user is a direction toward the viewer, wherein at least a component of the direction corresponding to the second user is perpendicular to an image plane of the arrangement.

In some aspects, generating the modified image data includes using one or more trained machine learning models to generate the modified image data at least in part by providing the image data and the gaze and the arrangement as inputs to the one or more trained machine learning models. In some aspects, the one or more trained machine learning models include a generative adversarial network.

In some aspects, one or more of the methods, apparatuses, and computer-readable medium described above further comprise: receiving second image data representing at least a portion of the second user as captured by a second image sensor. In some aspects, identifying that a second gaze of the second user as represented in the second image data is directed toward a second gaze area; generating modified second image data based on the second gaze and the arrangement at least in part by modifying the second image data to modify at least the portion of the second user in the second image data to be visually directed toward a direction corresponding to the second gaze area based on the second gaze and the arrangement; and outputting the modified second image data arranged according to the arrangement. In some aspects, generating the modified second image data includes using one or more trained machine learning models to generate the modified second image data at least in part by providing the second image data and the second gaze and the arrangement as inputs to the one or more trained machine learning models.

In some aspects, the second gaze area includes a displayed representation of at least the portion of the first user, wherein the direction corresponding to the second gaze area is a direction from a position of the modified second image data in the arrangement to a position of the modified image data in the arrangement, wherein at least a component of the direction corresponding to the second gaze area is parallel to an image plane of the arrangement. In some aspects, the second gaze area includes a displayed representation of at least a portion of a third user, wherein the direction corresponding to the second gaze area is a direction from a position of the modified second image data in the arrangement to a position of third image data representing the third user in the arrangement, wherein at least a component of the direction corresponding to the second gaze area is parallel to an image plane of the arrangement.

In some aspects, generating the modified image data includes: generating intermediate image data at least in part by modifying the image data to modify at least the portion of the first user in the image data to be visually directed toward a forward direction perpendicular to an image plane of the intermediate image data, and generating the modified image data at least in part by modifying the intermediate image data to modify at least the portion of the first user in the intermediate image data to be visually directed toward the direction corresponding to the second user.

In some aspects, identifying that the gaze of the first user as represented in the image data is directed toward the displayed representation of at least the portion of the second user includes analyzing the image data in comparison to a known position of the displayed representation of at least the portion of the second user.

In some aspects, one or more of the methods, apparatuses, and computer-readable medium described above further comprise: receiving prior image data representing at least the portion of the first user and a second portion of the first user, wherein the prior image data is captured by the first image sensor before capture of the image data by the first image sensor, wherein generating the modified image data includes incorporating at least some of the prior image data that represents the second portion of the first user into the modified image data.

In some aspects, generating the modified image data includes modifying the image data to modify at least the portion of the first user from a realistic form into an avatar form. In some aspects, the first user has a facial expression as represented in the image data, and wherein generating the modified image data includes modifying the avatar form to apply an indicator of the facial expression to the avatar form.

In some aspects, the first user has a facial expression as represented in the image data, and wherein generating the modified image data includes modifying the image data to modify at least the portion of the first user to mask the facial expression.

In some aspects, one or more of the methods, apparatuses, and computer-readable medium described above further comprise: a display, wherein outputting the modified image data arranged according to the arrangement includes displaying the modified image data using the display. In some aspects, one or more of the methods, apparatuses, and computer-readable medium described above further comprise: a communication interface, wherein outputting the modified image data arranged according to the arrangement includes sending the modified image data to a recipient device using the communication interface, wherein the recipient device renders the modified image data arranged according to the arrangement.

In some aspects, the apparatus is part of, and/or includes a wearable device, an extended reality device (e.g., a virtual reality (VR) device, an augmented reality (AR) device, or a mixed reality (MR) device), a head-mounted display (HMD) device, a wireless communication device, a mobile device (e.g., a mobile telephone and/or mobile handset and/or so-called "smart phone" or other mobile device), a camera, a personal computer, a laptop computer, a server computer, a vehicle or a computing device or component of a vehicle, another device, or a combination thereof. In some aspects, the apparatus includes a camera or multiple cameras for capturing one or more images. In some aspects, the apparatus further includes a display for displaying one or more images, notifications, and/or other displayable data. In some aspects, the apparatuses described above can include one or more sensors (e.g., one or more inertial measurement units (IMUs), such as one or more gyroscopes, one or more gyrometers, one or more accelerometers, any combination thereof, and/or other sensor).

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and aspects, will become more apparent upon referring to the following specification, claims, and accompanying drawings.

BRIEF DESCRIPTION OF THE DRAWINGS

Illustrative aspects of the present application are described in detail below with reference to the following drawing figures.

DETAILED DESCRIPTION

Figure 1:
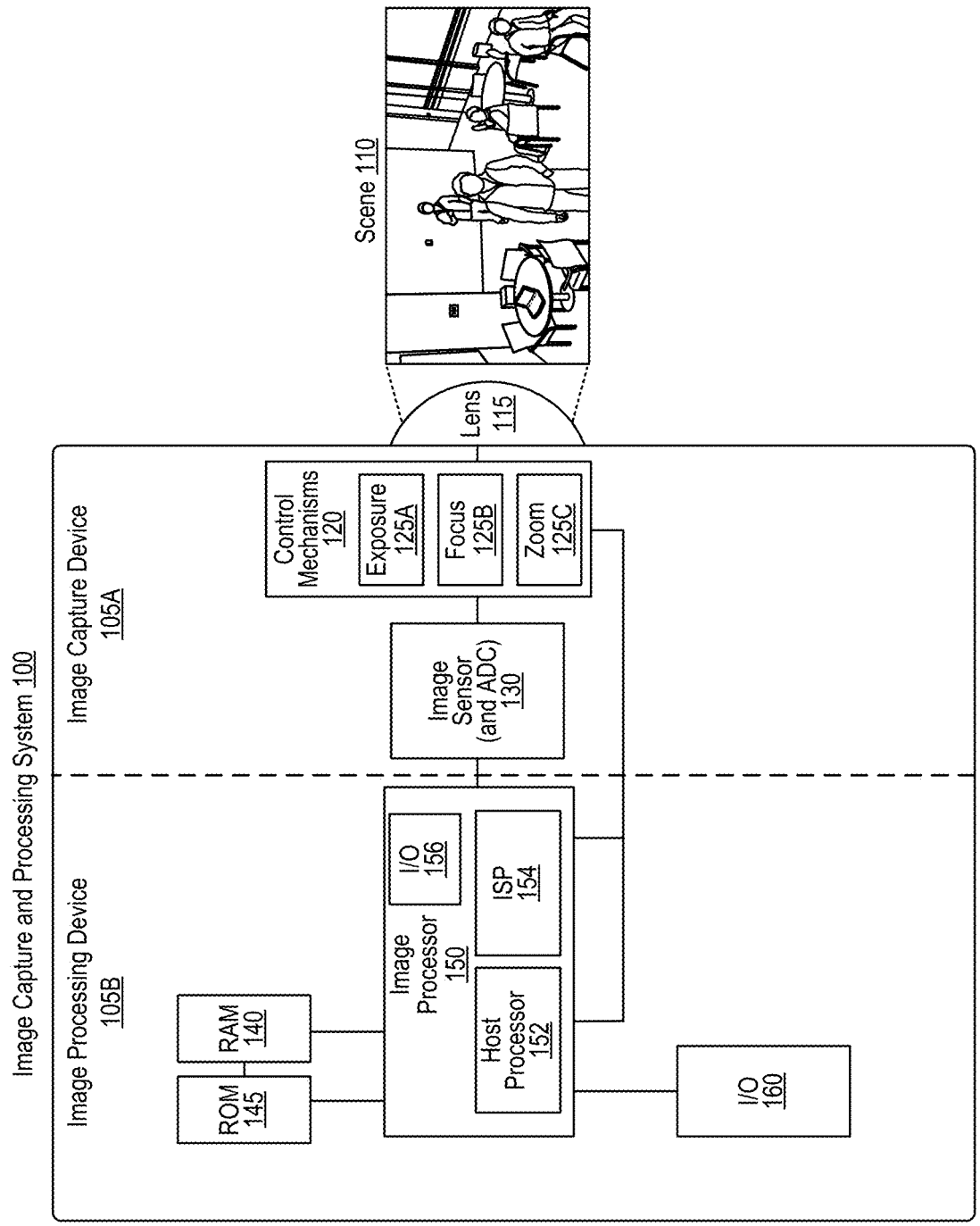
FIG. 1 is a block diagram illustrating an example architecture of an image capture and processing system, in accordance with some examples.

Certain aspects of this disclosure are provided below. Some of these aspects may be applied independently and some of them may be applied in combination as would be apparent to those of skill in the art. In the following description, for the purposes of explanation, specific details are set forth in order to provide a thorough understanding of aspects of the application. However, it will be apparent that various aspects may be practiced without these specific details. The figures and description are not intended to be restrictive.

The ensuing description provides example aspects only, and is not intended to limit the scope, applicability, or configuration of the disclosure. Rather, the ensuing description of the example aspects will provide those skilled in the art with an enabling description for implementing an example aspect. It should be understood that various changes may be made in the function and arrangement of elements without departing from the spirit and scope of the application as set forth in the appended claims.

A camera is a device that receives light and captures image frames, such as still images or video frames, using an image sensor. The terms "image," "image frame," and "frame" are used interchangeably herein. Cameras can be configured with a variety of image capture and image processing settings. The different settings result in images with different appearances. Some camera settings are determined and applied before or during capture of one or more image frames, such as ISO, exposure time, aperture size, f/stop, shutter speed, focus, and gain. For example, settings or parameters can be applied to an image sensor for capturing the one or more image frames. Other camera settings can configure post-processing of one or more image frames, such as alterations to contrast, brightness, saturation, sharpness, levels, curves, or colors. For example, settings or parameters can be applied to a processor (e.g., an image signal processor or ISP) for processing the one or more image frames captured by the image sensor.

Extended reality (XR) systems or devices can provide virtual content to a user and/or can combine real-world views of physical environments (scenes) and virtual environments (including virtual content). XR systems facilitate user interactions with such combined XR environments. The real-world view can include real-world objects (also referred to as physical objects), such as people, vehicles, buildings, tables, chairs, and/or other real-world or physical objects. XR systems or devices can facilitate interaction with different types of XR environments (e.g., a user can use an XR system or device to interact with an XR environment). XR systems can include virtual reality (VR) systems facilitating interactions with VR environments, augmented reality (AR) systems facilitating interactions with AR environments, mixed reality (MR) systems facilitating interactions with MR environments, and/or other XR systems. Examples of XR systems or devices include head-mounted displays (HMDs), smart glasses, among others. In some cases, an XR system can track parts of the user (e.g., a hand and/or fingertips of a user) to allow the user to interact with items of virtual content.

Video conferencing is a network-based technology that allows multiple users, who may each be in different locations, to connect in a video conference over a network using respective user devices that generally each include displays and cameras. In video conferencing, each camera of each user device captures image data representing the user who is using that user device, and sends that image data to the other user devices connected to the video conference, to be displayed on the display of the other users who use those other user devices. Meanwhile, the user device displays image data representing the other users in the video conference, captured by the respective cameras of the other user devices that those other users use to connect to the video conference. Video conferencing can be used by a group of users to virtually speak face-to-face while users are in different locations. Video conferencing can be a valuable way to users to virtually meet with each other despite travel restrictions, such as those related to a pandemic. Video conferencing can be performed using user devices that connect to each other, in some cases through one or more servers. In some examples, the user devices can include laptops, phones, tablet computers, mobile handsets, video game consoles, vehicle computers, desktop computers, wearable devices, televisions, media centers, XR systems, or other computing devices discussed herein.

At a true in-person meeting, it is generally visible who is looking where (e.g., at who) at a given moment, which can provide important context. On the other hand, a user in a video conference generally cannot see where (e.g., at who) other users in the video conference are looking. For instance, depictions of the same user may be arranged in different ways by the different user devices attending the video conference, so even if it is visible that a given user is looking at a specific portion of their screen, it can still be unclear who the user is looking at. In an illustrative example, an image of a first user may be displayed in an upper-left corner of a second user's screen, but may be displayed in a lower-right corner of a third user's screen, meaning that the second user and the third user can both be looking at the first user despite having different respective gaze directions.

In some examples, systems and techniques are described for image processing. An imaging system receives image data representation of the representing at least a portion (e.g., a face) of a first user as captured by a first image sensor. The imaging system identifies that a gaze of the first user as represented in the image data is directed toward a displayed representation of at least a portion of (e.g., a face) of a second user. For instance, the imaging system can determine that the gaze of the first user is on an upper-right corner of a display screen of the first user's device while the upper-right corner of the display screen of the first user's device is displaying an image of a second user—and therefore that the gaze of the first user is on the second user. The imaging system identifies an arrangement of representations of users for output (e.g., to be displayed using a display). For instance, the arrangement may include a grid of the representations of users, where each cell of the grid includes a different user's representation. The imaging system generates modified image data based on the gaze and the arrangement at least in part by modifying the image data to modify at least the portion (e.g., the face) of the first user to be visually directed toward a direction corresponding to the second user based on the gaze and the arrangement. In some examples, the imaging system uses one or more trained machine learning models to generate the modified image data based on the image data, the gaze, and/or the arrangement. For instance, if the second user is viewing the display, then in the modified image data, the first user can face the position of the second user while the second user views the display. If a third user is viewing the display, and the arrangement includes a representation of the second user then in the modified image data, the first user can face the position of the representation of the second user in the arrangement. The imaging system can output the modified image data according to the arrangement, for instance by causing a display to display the modified image data arranged according to the arrangement and/or by sending the modified image data to a recipient device.

The imaging systems and techniques described herein provide a number of technical improvements over prior imaging systems. For instance, the imaging systems and techniques described herein can provide additional functionality for video conferencing, allowing a user of a video conference to see where (e.g., at who or what) other users of the video conference are looking at a given moment. This can provide helpful context for conversations conducted over the video conference. The imaging systems and techniques described herein can provide additional privacy without losing this functionality, for instance by generating avatars for users and customizing the avatars to indicate where (e.g., at who or what) the users of the video conference are looking at a given moment. In some examples, the imaging systems and techniques described herein can pass user facial expressions on to the avatar to preserve expressiveness while protecting privacy. In some examples, imaging systems and techniques described herein can mask user facial expressions in an avatar representation of the user or in a realistic camera-based representation of the user, also protecting the user's privacy.

Figure 2:
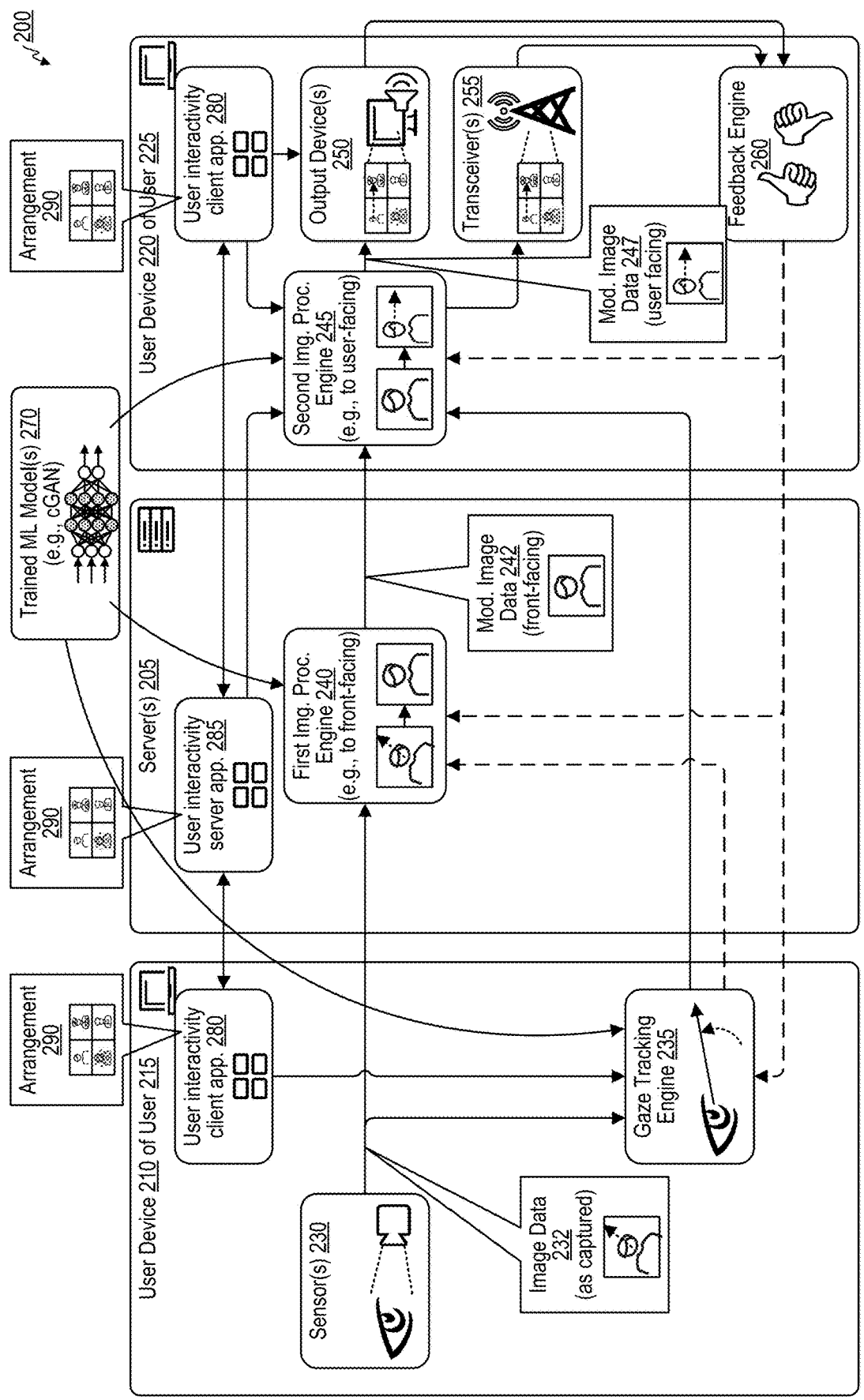
FIG. 2 is a block diagram illustrating an example architecture of an imaging system performing an imaging process, in accordance with some examples.

Various aspects of the application will be described with respect to the figures. FIG. 1 is a block diagram illustrating an architecture of an image capture and processing system 100. The image capture and processing system 100 includes various components that are used to capture and process images of one or more scenes (e.g., an image of a scene 110). The image capture and processing system 100 can capture standalone images (or photographs) and/or can capture videos that include multiple images (or video frames) in a particular sequence. A lens 115 of the system 100 faces a scene 110 and receives light from the scene 110. The lens 115 bends the light toward the image sensor 130. The light received by the lens 115 passes through an aperture controlled by one or more control mechanisms 120 and is received by an image sensor 130. In some examples, the scene 110 is a scene in an environment. In some examples, the scene 110 is a scene of at least a portion of a user, such as the user that the sensors 230 of FIG. 2 are facing. For instance, the scene 110 can be a scene of one or both of the user's eyes, and/or at least a portion of the user's face.

The one or more control mechanisms 120 may control exposure, focus, and/or zoom based on information from the image sensor 130 and/or based on information from the image processor 150. The one or more control mechanisms 120 may include multiple mechanisms and components; for instance, the control mechanisms 120 may include one or more exposure control mechanisms 125A, one or more focus control mechanisms 125B, and/or one or more zoom control mechanisms 125C. The one or more control mechanisms 120 may also include additional control mechanisms besides those that are illustrated, such as control mechanisms controlling analog gain, flash, HDR, depth of field, and/or other image capture properties.

The focus control mechanism 125B of the control mechanisms 120 can obtain a focus setting. In some examples, focus control mechanism 125B store the focus setting in a memory register. Based on the focus setting, the focus control mechanism 125B can adjust the position of the lens 115 relative to the position of the image sensor 130. For example, based on the focus setting, the focus control mechanism 125B can move the lens 115 closer to the image sensor 130 or farther from the image sensor 130 by actuating a motor or servo, thereby adjusting focus. In some cases, additional lenses may be included in the system 100, such as one or more microlenses over each photodiode of the image sensor 130, which each bend the light received from the lens 115 toward the corresponding photodiode before the light reaches the photodiode. The focus setting may be determined via contrast detection autofocus (CDAF), phase detection autofocus (PDAF), or some combination thereof. The focus setting may be determined using the control mechanism 120, the image sensor 130, and/or the image processor 150. The focus setting may be referred to as an image capture setting and/or an image processing setting.

The exposure control mechanism 125A of the control mechanisms 120 can obtain an exposure setting. In some cases, the exposure control mechanism 125A stores the exposure setting in a memory register. Based on this exposure setting, the exposure control mechanism 125A can control a size of the aperture (e.g., aperture size or f/stop), a duration of time for which the aperture is open (e.g., exposure time or shutter speed), a sensitivity of the image sensor 130 (e.g., ISO speed or film speed), analog gain applied by the image sensor 130, or any combination thereof. The exposure setting may be referred to as an image capture setting and/or an image processing setting.

The zoom control mechanism 125C of the control mechanisms 120 can obtain a zoom setting. In some examples, the zoom control mechanism 125C stores the zoom setting in a memory register. Based on the zoom setting, the zoom control mechanism 125C can control a focal length of an assembly of lens elements (lens assembly) that includes the lens 115 and one or more additional lenses. For example, the zoom control mechanism 125C can control the focal length of the lens assembly by actuating one or more motors or servos to move one or more of the lenses relative to one another. The zoom setting may be referred to as an image capture setting and/or an image processing setting. In some examples, the lens assembly may include a parfocal zoom lens or a varifocal zoom lens. In some examples, the lens assembly may include a focusing lens (which can be lens 115 in some cases) that receives the light from the scene 110 first, with the light then passing through an afocal zoom system between the focusing lens (e.g., lens 115) and the image sensor 130 before the light reaches the image sensor 130. The afocal zoom system may, in some cases, include two positive (e.g., converging, convex) lenses of equal or similar focal length (e.g., within a threshold difference) with a negative (e.g., diverging, concave) lens between them. In some cases, the zoom control mechanism 125C moves one or more of the lenses in the afocal zoom system, such as the negative lens and one or both of the positive lenses.

The image sensor 130 includes one or more arrays of photodiodes or other photosensitive elements. Each photodiode measures an amount of light that eventually corresponds to a particular pixel in the image produced by the image sensor 130. In some cases, different photodiodes may be covered by different color filters, and may thus measure light matching the color of the filter covering the photodiode. For instance, Bayer color filters include red color filters, blue color filters, and green color filters, with each pixel of the image generated based on red light data from at least one photodiode covered in a red color filter, blue light data from at least one photodiode covered in a blue color filter, and green light data from at least one photodiode covered in a green color filter. Other types of color filters may use yellow, magenta, and/or cyan (also referred to as "emerald") color filters instead of or in addition to red, blue, and/or green color filters. Some image sensors may lack color filters altogether, and may instead use different photodiodes throughout the pixel array (in some cases vertically stacked). The different photodiodes throughout the pixel array can have different spectral sensitivity curves, therefore responding to different wavelengths of light. Monochrome image sensors may also lack color filters and therefore lack color depth.

In some cases, the image sensor 130 may alternately or additionally include opaque and/or reflective masks that block light from reaching certain photodiodes, or portions of certain photodiodes, at certain times and/or from certain angles, which may be used for phase detection autofocus (PDAF). The image sensor 130 may also include an analog gain amplifier to amplify the analog signals output by the photodiodes and/or an analog to digital converter (ADC) to convert the analog signals output of the photodiodes (and/or amplified by the analog gain amplifier) into digital signals. In some cases, certain components or functions discussed with respect to one or more of the control mechanisms 120 may be included instead or additionally in the image sensor 130. The image sensor 130 may be a charge-coupled device (CCD) sensor, an electron-multiplying CCD (EMCCD) sensor, an active-pixel sensor (APS), a complimentary metal-oxide semiconductor (CMOS), an N-type metal-oxide semiconductor (NMOS), a hybrid CCD/CMOS sensor (e.g., sCMOS), or some other combination thereof The image processor 150 may include one or more processors, such as one or more image signal processors (ISPs) (including ISP 154), one or more host processors (including host processor 152), and/or one or more of any other type of processor 810 discussed with respect to the computing system 800. The host processor 152 can be a digital signal processor (DSP) and/or other type of processor. In some implementations, the image processor 150 is a single integrated circuit or chip (e.g., referred to as a system-on-chip or SoC) that includes the host processor 152 and the ISP 154. In some cases, the chip can also include one or more input/output ports (e.g., input/output (I/O) ports 156), central processing units (CPUs), graphics processing units (GPUs), broadband modems (e.g., 3 G, 4 G or LTE, 5 G, etc.), memory, connectivity components (e.g., Bluetooth™, Global Positioning System (GPS), etc.), any combination thereof, and/or other components. The I/O ports 156 can include any suitable input/output ports or interface according to one or more protocol or specification, such as an Inter-Integrated Circuit 2 (I2C) interface, an Inter-Integrated Circuit 3 (I3C) interface, a Serial Peripheral Interface (SPI) interface, a serial General Purpose Input/Output (GPIO) interface, a Mobile Industry Processor Interface (MIPI) (such as a MIPI CSI-2 physical (PHY) layer port or interface, an Advanced High-performance Bus (AHB) bus, any combination thereof, and/or other input/output port. In one illustrative example, the host processor 152 can communicate with the image sensor 130 using an I2C port, and the ISP 154 can communicate with the image sensor 130 using an MIPI port.

The image processor 150 may perform a number of tasks, such as de-mosaicing, color space conversion, image frame downsampling, pixel interpolation, automatic exposure (AE) control, automatic gain control (AGC), CDAF, PDAF, automatic white balance, merging of image frames to form an HDR image, image recognition, object recognition, feature recognition, receipt of inputs, managing outputs, managing memory, or some combination thereof. The image processor 150 may store image frames and/or processed images in random access memory (RAM) 140 and/or 820, read-only memory (ROM) 145 and/or 825, a cache, a memory unit, another storage device, or some combination thereof.

Various input/output (I/O) devices 160 may be connected to the image processor 150. The I/O devices 160 can include a display screen, a keyboard, a keypad, a touchscreen, a trackpad, a touch-sensitive surface, a printer, any other output devices 835, any other input devices 845, or some combination thereof In some cases, a caption may be input into the image processing device 105B through a physical keyboard or keypad of the I/O devices 160, or through a virtual keyboard or keypad of a touchscreen of the I/O devices 160. The I/O 160 may include one or more ports, jacks, or other connectors that enable a wired connection between the system 100 and one or more peripheral devices, over which the system 100 may receive data from the one or more peripheral device and/or transmit data to the one or more peripheral devices. The I/O 160 may include one or more wireless transceivers that enable a wireless connection between the system 100 and one or more peripheral devices, over which the system 100 may receive data from the one or more peripheral device and/or transmit data to the one or more peripheral devices. The peripheral devices may include any of the previously-discussed types of I/O devices 160 and may themselves be considered I/O devices 160 once they are coupled to the ports, jacks, wireless transceivers, or other wired and/or wireless connectors.

In some cases, the image capture and processing system 100 may be a single device. In some cases, the image capture and processing system 100 may be two or more separate devices, including an image capture device 105A (e.g., a camera) and an image processing device 105B (e.g., a computing device coupled to the camera). In some implementations, the image capture device 105A and the image processing device 105B may be coupled together, for example via one or more wires, cables, or other electrical connectors, and/or wirelessly via one or more wireless transceivers. In some implementations, the image capture device 105A and the image processing device 105B may be disconnected from one another.

As shown in FIG. 1, a vertical dashed line divides the image capture and processing system 100 of FIG. 1 into two portions that represent the image capture device 105A and the image processing device 105B, respectively. The image capture device 105A includes the lens 115, control mechanisms 120, and the image sensor 130. The image processing device 105B includes the image processor 150 (including the ISP 154 and the host processor 152), the RAM 140, the ROM 145, and the I/O 160. In some cases, certain components illustrated in the image capture device 105A, such as the ISP 154 and/or the host processor 152, may be included in the image capture device 105A.

The image capture and processing system 100 can include an electronic device, such as a mobile or stationary telephone handset (e.g., smartphone, cellular telephone, or the like), a desktop computer, a laptop or notebook computer, a tablet computer, a set-top box, a television, a camera, a display device, a digital media player, a video gaming console, a video streaming device, an Internet Protocol (IP) camera, or any other suitable electronic device. In some examples, the image capture and processing system 100 can include one or more wireless transceivers for wireless communications, such as cellular network communications, 802.11 wi-fi communications, wireless local area network (WLAN) communications, or some combination thereof. In some implementations, the image capture device 105A and the image processing device 105B can be different devices. For instance, the image capture device 105A can include a camera device and the image processing device 105B can include a computing device, such as a mobile handset, a desktop computer, or other computing device.

While the image capture and processing system 100 is shown to include certain components, one of ordinary skill will appreciate that the image capture and processing system 100 can include more components than those shown in FIG. 1. The components of the image capture and processing system 100 can include software, hardware, or one or more combinations of software and hardware. For example, in some implementations, the components of the image capture and processing system 100 can include and/or can be implemented using electronic circuits or other electronic hardware, which can include one or more programmable electronic circuits (e.g., microprocessors, GPUs, DSPs, CPUs, and/or other suitable electronic circuits), and/or can include and/or be implemented using computer software, firmware, or any combination thereof, to perform the various operations described herein. The software and/or firmware can include one or more instructions stored on a computer-readable storage medium and executable by one or more processors of the electronic device implementing the image capture and processing system 100.

FIG. 2 is a block diagram illustrating an example architecture of an imaging system 200 performing an imaging process. The imaging system 200, and the corresponding imaging process, can be used in video conferencing, extended reality (XR), video gaming, metaverse environments, or combinations thereof.

The imaging system 200 includes one or more servers 205, a user device 210 of a user 215, and a user device 220 of a user 225. Each of the server(s) 205, the user device 210, and/or the user device 220 can include at least one computing system 800. Each of the server(s) 205, the user device 210, and/or the user device 220 can include, for instance, one or more laptops, phones, tablet computers, mobile handsets, video game consoles, vehicle computers, desktop computers, wearable devices, televisions, media centers, XR systems, or other computing devices discussed herein, or combinations thereof. In some examples, the user device 210 includes the components illustrated as included in the user device 220. In some examples, the user device 210 can perform the operations illustrated as performed by the user device 220. In some examples, the user device 220 includes the components illustrated as included in the user device 210. In some examples, the user device 220 can perform the operations illustrated as performed by the user device 210. The imaging system 200 includes one or more trained machine learning (ML) models 270. Each of the server(s) 205, the user device 210, and/or the user device 220 can include at least one of the trained ML model(s) 270. In some examples, the imaging system 200 includes one or more additional devices that include at least one of the trained ML model(s) 270.

In some examples, the imaging system 200 includes user interactivity software application. The user interactivity software application includes one more instances of a user interactivity client application 280 and a user interactivity server application 285. For instance, the user device 210 of the user 215 includes a first instance of the user interactivity client application 280, while the user device 220 of the user 225 includes a second instance of the user interactivity client application 280. One or more of the server(s) 205 can include a respective instance of the user interactivity server application 285. The user interactivity software application—including the instance(s) of the user interactivity client application 280 and the user interactivity server application 285—can include software application(s) for video conferencing, teleconferencing, extended reality (XR), video gaming, metaverse environments, or combinations thereof. In some examples, the instance(s) of the user interactivity client application 280 and the user interactivity server application 285 can determine and/or generate an arrangement 290 of representations of users, such as image(s) of users. In some examples, the arrangement 290 can include a grid or lattice of representations of users. In some examples, the arrangement 290 can include a three-dimensional (3 D) environment that includes representations of users, as in a video game, extended reality environment, metaverse environment, or a combination thereof.

The user device 210 of the user 215 includes one or more sensors 230. In some examples, the sensor(s) 230 capture sensor data measuring and/or tracking information about aspects of the user 215's body and/or behaviors by the user 215. In some examples, the sensors 230 include one or more image sensors of one or more cameras that face at least a portion of the user (e.g., at least a portion of the face and/or head of the user 215). The one or more cameras can include one or more image sensors that capture image data 232 including one or more images of at least a portion of the user 215. For instance, the sensors 230 can include one or more image sensors focused on one or both eyes (and/or eyelids) of the user 215, with the image sensors of the cameras capturing image data 232 of one or both eyes of the user 215. The one or more image sensors may also be referred to as eye capturing sensor(s). In some implementations, the one or more image sensors can capture image data 232 that includes series of images over time, which in some examples may be sequenced together in temporal order, for instance into videos. These series of images can depict or otherwise indicate, for instance, movements of the user 215's eye(s), pupil dilations, blinking (using the eyelids), squinting (using the eyelids), saccades, fixations, eye moisture levels, optokinetic reflexes or responses, vestibulo-ocular reflexes or responses, accommodation reflexes or responses, other attributes related to eyes and/or eyelids described herein, or a combination thereof. Within FIG. 2, the one or more sensors 230 are illustrated as a camera facing an eye of the user 215 and capturing image data 232 of at least an eye of the user 215. In some examples, the sensor(s) 230 can be referred to as user-facing sensors or user-focused sensors.

The sensors 230 can include one or more sensors that track information about the user 215's body and/or behaviors, such as one or more cameras, image sensors, microphones, heart rate monitors, oximeters, biometric sensors, positioning receivers, Global Navigation Satellite System (GNSS) receivers, Inertial Measurement Units (IMUs), accelerometers, gyroscopes, gyrometers, barometers, thermometers, altimeters, depth sensors, light detection and ranging (LIDAR) sensors, radio detection and ranging (RADAR) sensors, sound detection and ranging (SODAR) sensors, sound navigation and ranging (SONAR) sensors, time of flight (ToF) sensors, structured light sensors, other sensors discussed herein, or combinations thereof In some examples, the one or more sensors 230 include at least one image capture and processing system 100, image capture device 105A, image processing device 105B, or combination(s) thereof. In some examples, the one or more sensors 230 include at least one input device 845 of the computing system 800. In some implementations, one or more of the sensor(s) 230 may complement or refine sensor readings from other sensor(s) 230. For example, Inertial Measurement Units (IMUs), accelerometers, gyroscopes, or other sensors may be used by the gaze tracking engine 235 to refine the determination of the user 215's gaze.

The user device 210 of the user 215 includes gaze tracking engine 235 that receives the image data 232 from the sensors 230 and determines a gaze of the user 215 based on the image data 232. The gaze tracking engine 235 can provide the image data 232 as input(s) to the trained ML model(s) 270 to perform, on the image data 232, feature detection, feature extraction, feature recognition, feature tracking, object detection, object recognition, object tracking, facial detection, facial recognition, facial tracking, person detection, person recognition, person tracking, or a combination thereof. The gaze tracking engine 235 can use these techniques to detect, recognize, and/or track a person (e.g., the user 215), a face of a person (e.g., the user 215), one or both eyes of the person (e.g., the user 215), and/or pupil(s) of one or both eyes of the person (e.g., the user 215). By detecting, recognizing, and/or tracking these aspects of the user 215, the gaze tracking engine 235 identifies a gaze direction and/or gaze area for the user 215 as depicted and/or otherwise represented in the image data 232. The gaze direction identifies a direction of the gaze of the user 215, for instance identified as a vector extending from the pupil(s) of the eye(s) of the user 215. The gaze area identifies an area of the environment that the user 215 is in that the gaze of the user 215 is directed at or toward, indicating what object and/or content in the environment the gaze of the user 215 is looking at.

In some examples, the gaze tracking engine 235 can perform one or more transformations on the gaze that the gaze tracking engine 235 determines from the image data 232 as discussed above. The one or more transformations performed by the gaze tracking engine 235 can convert a gaze direction (e.g., gaze vector) determined from the image data 232 (e.g., that may be expressed in terms of and/or relative to pixel coordinates in the image data 232) into a gaze direction (e.g., gaze vector) in the real-world environment in which the user 215 is in (e.g., that may be expressed in terms of and/or relative to 3 D coordinates in the real-world environment in which the user 215 is in). The gaze direction can be represented as a gaze vector starting from a position of the eye(s) of the user 215 in the real-world environment and directed toward the direction of the user 215's gaze. In some examples, the one or more transformations can be performed based on a distance between at least one of the sensor(s) 230 and the user 215. This distance may be measured, for instance using one or more range sensor(s) (e.g., RADAR sensor(s), LIDAR sensor(s), SONAR sensor(s), SODAR sensor(s), ToF sensor(s), structured light sensor(s), infrared sensor(s), ultrasound sensor(s), and/or rangefinder(s)) of the sensor(s) 230. This distance may be measured, for instance by comparing size of one or more body parts (e.g., head, eye, nose, mouth) of the user 215 in the image data 232 to average sizes of the one or more body parts, by comparing a distance between two or more body parts (e.g., inter-eye distance) of the user 215 in the image data 232 to average distances between two or more body parts, or a combination thereof. In some examples, the gaze tracking engine 235 can use the trained ML model(s) 270 to generate the one or more transformations and/or to transform the gaze direction (e.g., gaze vector) determined from the image data 232 into the gaze direction (e.g., gaze vector) in the real-world environment in which the user 215 is in, as discussed above. For instance, the gaze tracking engine 235 can receive the gaze direction (e.g., gaze vector) in the real-world environment in which the user 215 is in as an output from the trained ML model(s) 270 in response to input, into the trained ML model(s) 270, of inputs that include at least one of the image data 232, gaze direction (e.g., gaze vector) determined from the image data 232, the gaze direction (e.g., gaze vector) determined from the image data 232 (e.g., that may be expressed in terms of and/or relative to pixel coordinates in the image data 232), the measured or estimated distance between the user and at least one of the sensor(s) 230, or a combination thereof.

In some examples, the gaze tracking engine 235 determines the gaze direction to be directed at a portion of a display of the user device 210 (e.g., a display coupled to the user device 210) while content is displayed on the display. In some examples, the gaze tracking engine 235 determines the gaze area to be a portion of the display of the user device 210 (e.g., a display coupled to the user device 210) while content is displayed on the display. To do so, the gaze tracking engine 235 can, for instance, determine the 3 D position of eye(s) of the user 215 in the real-world environment, determine the gaze direction of the user 215 in the real-world environment as discussed above, determine the 3 D position of the display relative to the user in the real-world environment, determine a direction from the position of the eye(s) of the user 215 to the position of the display (e.g., to be compared to the user 215's gaze direction), determine the portion of the display (e.g., the location on the display) at which the content is being displayed on the display, determine a direction from the position of the eye(s) of the user 215 to the position of the displayed content being displayed on the display (to be compared to the user 215's gaze direction), or a combination thereof. The content displayed on the display can include representations of other users, such as the user 225, positioned in an arrangement 290 that is determined using the instance of the user interactivity client application 280 run by the user device 210. The gaze tracking engine 235 can identify, based on the gaze direction, the gaze area, and/or the arrangement 290 from the instance of the user interactivity client application 280 run by the user device 210, which of the representations of the other users in the arrangement 290 (of the user interactivity client application 280) the gaze of the user 215 is looking at or directed toward. In some examples, pose sensors of the sensor(s) 230, such as the Inertial Measurement Units (IMUs), accelerometers, and/or gyroscopes, may be used by the gaze tracking engine 235 to refine the determination of the user 215's gaze, for instance if the user device 210 is a head-mounted display (HMD) device (e.g., HMD 310) and/or the pose sensors track the orientation (e.g., pitch, yaw, and/or roll) of the head of the user.

The server(s) 205 receive the image data 132 from the user device 210, which can send the image data 132 to the server(s) 205. The server(s) 205 include a first image processing engine 240 that can process (e.g., modify) the image data 232 of the user 215 to generate the modified image data 242 of the user 215. To generate the modified image data 242, the first image processing engine 240 modifies the image data 232 to straighten and/or level the depiction of the user 215, to depict the user 215 as if the eyes and/or face and/or body of the user 215 were directed toward the camera that captured the image data 232 (e.g., perpendicular to the image plane), to increase image resolution of the image data 232 from a first resolution to a second resolution using super-resolution. to decrease image resolution of the image data 232 from a first resolution to a second resolution to reduce bandwidth usage, to compress the image data 232 using still image compression and/or video compression techniques to reduce bandwidth usage, to adjust brightness, to adjust contrast, to adjust gamma, to adjust tone, to adjust luminance, to adjust color saturation, to adjust color mapping, to adjust color channel mixing, to adjust sharpness, to adjust blurring, or a combination thereof. The first image processing engine 240 can use the trained ML model(s) 270 to process (e.g., modify) the image data 232 of the user 215 to generate the modified image data 242 of the user 215. For instance, the server(s) 205 can provide the image data 132 to the trained ML model(s) 270 of the first image processing engine 240, and the trained ML model(s) 270 of the first image processing engine 240 can generate the modified image data 242 based on the image data 132. In some examples, the server(s) 205 can also provide gaze data from the gaze tracking engine 235 to the trained ML model(s) 270 of the first image processing engine 240, and the trained ML model(s) 270 of the first image processing engine 240 generate the modified image data 242 based on the image data 132 and the gaze data.

The box representing the image data 232 in FIG. 2 includes an illustrative example of the image data 232. The illustrative example of the image data 232 is depicted as an image of the user 215 where the user 215 appears skewed (the user 215 appears tilted slightly clockwise) and where the face of the user 215 appears to be angled to be looking slightly up (as represented by the dashed arrow pointing up relative to the representation of the user 215 and the distortion of the representation of the user 215). The box representing the modified image data 242 in FIG. 2 includes an illustrative example of the modified image data 242. The illustrative example of the modified image data 242 appears straightened relative to the image data 232 (e.g., no longer skewed or tilted clockwise), and the face of the user 215 in the modified image data 242 appears to face toward the camera that captured the image data 232. In some examples, the eye(s) of the user 215 may look in a direction other than toward the camera in the image data 232, but can be modified in the modified image data 242 (by the first image processing engine 240) to look toward the camera. Further examples of the image data 232 are illustrated in the input face image data 505 of FIG. 5. Further examples of the modified image data 242 are illustrated in the front-facing face image data 510 of FIG. 5.

The user device 220 of the user 225 receives the modified image data 242 from the server(s) 205. In some examples, the user device 220 of the user 225 receives the image data 132 from the user device 210 and/or the server(s) 205 instead of or in addition to the modified image data 242. The user device 220 includes a second image processing engine 245 that can process (e.g., modify) the modified image data 242 and/or the image data 232 of the user 215 to generate the modified image data 247 of the user 215 based on gaze information from the gaze tracking engine 235. The gaze information can identify what, or who, the user 215 is looking at based on the analysis of image data 232 by the gaze tracking engine 235. To generate the modified image data 247, the second image processing engine 245 modifies the image data 232 and/or the modified image data 242 to depict the body of the of the user 215 as if the body of the user 215 was facing toward the object or person that the user 215 is looking at based on the gaze information, to depict the face of the user 215 as if the face of the user 215 was facing toward the object or person that the user 215 is looking at based on the gaze information, and/or to depict the eye(s) of the user 215 as if the eye(s) of the user 215 were facing toward the object or person that the user 215 is looking at based on the gaze information.

The second image processing engine 245 generates the modified image data 247 based on the gaze information so that the representation of the user in the modified image data 247 appears to be looking at the person or object that the gaze information identifies the user 215 as looking at. For instance, if the gaze information identifies that the user 215 is looking at a representation of the user 225 that is displayed on a display of the user device 210 (e.g., by the instance of the user interactivity client application 280 running on the user device 210), then the second image processing engine 245 generates the modified image data 242 of the user 215 so that the user 215 appears to be looking out of a display of the user device 220 toward the user 225 as the user 225 is viewing the display of the user device 220. In some examples, the second image processing engine 245 generates the modified image data 247 of the user 215 based also on the arrangement 290 of representations of users from the instance of the user interactivity clientapplication 280 running on the user device 220. For instance, if the gaze information identifies that the user 215 is looking at a representation of a third user (other than the user 215 and the user 225) that is displayed on a display of the user device 210 (e.g., by the instance of the user interactivity client application 280 running on the user device 210), then the second image processing engine 245 generates the modified image data 242 of the user 215 so that the user 215 appears to be looking up, down, to the side, or diagonally toward another representation of the third user is displayed on a display of the user device 220 according to the arrangement 290 of representations of users from the instance of the user interactivity client application 280 running on the user device 220. For instance, if the arrangement 290 of representations of users from the instance of the user interactivity client application 280 running on the user device 220 indicates that a representation of the third user should be arranged to the right of a representation of the user 215, then the second image processing engine 245 generates the modified image data 247 of the user 215 so that the user 215 appears to be looking to the right toward the representation of the third user.

The box representing the modified image data 247 in FIG. 2 includes an illustrative example of the modified image data 247. In the illustrative example of the modified image data 247, the user 215 appears to be looking to the right based on the dashed arrow to the right and the distortion of the representation of the user 215 that makes the user 215 appear tilted to the right. In an illustrative example, the gaze information can indicate that the user 215 is looking at a representation of a third user, and the arrangement 290 of representations of users from the instance of the user interactivity client application 280 running on the user device 220 indicates that a representation of the third user should be arranged to the right of a representation of the user 215. In the modified image data 247, the body, face, and/or eye(s) of the user 215 can appear to be facing and/or looking toward the representation of the third user. In a second example, the gaze information can indicate that the user 215 is looking at the user 225 while the user 225 is viewing a display of the user device 220, and the user 225 is positioned to the right of the representation of the user 215. In the modified image data 247, the body, face, and/or eye(s) of the user 215 can appear to be facing and/or looking toward the second user. Additional examples of the modified image data 247 include the output face image data 515 for user A 535 of FIG. 5, the output face image data 520 for user B 540 of FIG. 5, and the output face image data 525 for user C 545 of FIG. 5.

In some examples, to generate the modified image data 242, the first image processing engine 240 modifies the image data 232 to modify the representations of the faces of one or more users (e.g., the face of the user 215) from a realistic form into an avatar form. In some examples, to generate the modified image data 247, the second image processing engine 245 modifies the image data 232 and/or the modified image data 242 to modify the representations of the faces of one or more users (e.g., the face of the user 215) from a realistic form into an avatar form. For instance, use of the avatar forms of the user 215 can be used in instances where the user device 210 does not include an image sensor in its sensor(s) 230 and/or in instances where the user 215 authorizes the image data 232 to be used by the gaze tracking engine 235 (and/or the rest of the user device 210) but does not authorize (or expressly prohibits) access to, and/or use of, the image data 232 by the server(s) 205 and/or the user device 220. This can provide increased privacy and/or for the user 215.

The user device 220 includes output device(s) 250. The output device(s) 250 can include one or more visual output devices, such as display(s) or connector(s) therefor. The output device(s) 250 can include one or more audio output devices, such as speaker(s), headphone(s), and/or connector(s) therefor. The output device(s) 250 can include one or more of the output device 835 and/or of the communication interface 840 of the computing system 800. The user device 220 causes the display(s) of the output device 250 to display the modified image data 247 arranged according to the arrangement 290 of representations of users from the instance of the user interactivity client application 280 running on the user device 220.

In some examples, the user device 220 includes one or more transceivers 255. The transceiver(s) 255 can include wired transmitters, receivers, transceivers, or combinations thereof. The transceiver(s) 255 can include wireless transmitters, receivers, transceivers, or combinations thereof. The transceiver(s) 255 can include one or more of the output device 835 and/or of the communication interface 840 of the computing system 800. In some examples, the user device 220 causes the transceiver(s) 255 to send, to a recipient device, the modified image data 247 arranged according to the arrangement 290 of representations of users from the instance of the user interactivity client application 280 running on the user device 220. The recipient device can include a display, and the data sent to the recipient device from the user device 220 using the transceiver(s) 255 can cause the display of the recipient device to display the modified image data 247 arranged according to the arrangement 290 of representations of users from the instance of the user interactivity client application 280 running on the user device 220.

In some examples, the display(s) of the output device(s) 250 of the imaging system 200 function as optical "see-through" display(s) that allow light from the real-world environment (scene) around the imaging system 200 to traverse (e.g., pass) through the display(s) of the output device(s) 250 to reach one or both eyes of the user. For example, the display(s) of the output device(s) 250 can be at least partially transparent, translucent, light-permissive, light-transmissive, or a combination thereof. In an illustrative example, the display(s) of the output device(s) 250 includes a transparent, translucent, and/or light-transmissive lens and a projector. The display(s) of the output device(s) 250 of can include a projector that projects the virtual content onto the lens. The lens may be, for example, a lens of a pair of glasses, a lens of a goggle, a contact lens, a lens of a head-mounted display (HMD) device, or a combination thereof. Light from the real-world environment passes through the lens and reaches one or both eyes of the user. The projector can project virtual content (e.g., the modified image data 247 arranged according to the arrangement 290 of representations of users from the instance of the user interactivity client application 280 running on the user device 220) onto the lens, causing the virtual content to appear to be overlaid over the user's view of the environment from the perspective of one or both of the user's eyes. In some examples, the projector can project the virtual content onto the onto one or both retinas of one or both eyes of the user rather than onto a lens, which may be referred to as a virtual retinal display (VRD), a retinal scan display (RSD), or a retinal projector (RP) display.

In some examples, the display(s) of the output device(s) 250 of the imaging system 200 are digital "pass-through" display that allow the user of the imaging system 200 to see a view of an environment by displaying the view of the environment on the display(s) of the output device(s) 250. The view of the environment that is displayed on the digital pass-through display can be a view of the real-world environment around the imaging system 200, for example based on sensor data (e.g., images, videos, depth images, point clouds, other depth data, or combinations thereof) captured by one or more environment-facing sensors of the sensor(s) 230. The view of the environment that is displayed on the digital pass-through display can be a virtual environment (e.g., as in VR), which may in some cases include elements that are based on the real-world environment (e.g., boundaries of a room). The view of the environment that is displayed on the digital pass-through display can be an augmented environment (e.g., as in AR) that is based on the real-world environment. The view of the environment that is displayed on the digital pass-through display can be a mixed environment (e.g., as in MR) that is based on the real-world environment. The view of the environment that is displayed on the digital pass-through display can include virtual content (e.g., the modified image data 247 arranged according to the arrangement 290 of representations of users from the instance of the user interactivity client application 280 running on the user device 220) overlaid over other otherwise incorporated into the view of the environment.

The trained ML model(s) 270 can include include one or more neural network (NNs) (e.g., neural network 600), one or more convolutional neural networks (CNNs), one or more trained time delay neural networks (TDNNs), one or more deep networks, one or more autoencoders, one or more deep belief nets (DBNs), one or more recurrent neural networks (RNNs), one or more generative adversarial networks (GANs), one or more conditional generative adversarial networks (cGANs), one or more other types of neural networks, one or more trained support vector machines (SVMs), one or more trained random forests (RFs), one or more computer vision systems, one or more deep learning systems, or combinations thereof.

In some examples, the imaging system 200 includes a feedback engine 260. The feedback engine 260 is illustrated as part of the user device 220, but may additionally or alternatively be part of the user device 210 and/or the server(s) 205. The feedback engine 260 can detect feedback received from a user interface of the user device 220, the user device 210, and/or the server(s) 205. The feedback may include feedback on the modified image data 247 as displayed (e.g., using the display(s) of the output device(s) 250) according to the arrangement 290 of representations of users from the instance of the user interactivity client application 280 running on the user device 220. The feedback may include feedback on the modified image data 247 on its own. The feedback may include feedback on the modified image data 242. The feedback may include feedback on the gaze information generated by the gaze tracking engine 235. The feedback may include feedback on the second image processing engine 245, the first image processing engine 240, the gaze tracking engine 235, the trained ML model(s) 270, or a combination thereof. The feedback engine 260 can detect feedback about one engine of the imaging system 200 received from another engine of the imaging system 200, for instance whether one engine decides to use data from the other engine or not. The feedback received by the feedback engine 260 can be positive feedback or negative feedback. For instance, if the one engine of the imaging system 200 uses data from another engine of the imaging system 200, or if positive feedback from a user is received through a user interface, the feedback engine 260 can interpret this as positive feedback. If the one engine of the imaging system 200 declines to data from another engine of the imaging system 200, or if negative feedback from a user is received through a user interface, the feedback engine 260 can interpret this as negative feedback. Positive feedback can also be based on attributes of the sensor data from the sensor(s) 230, such as the user smiling, laughing, nodding, saying a positive statement (e.g., "yes," "confirmed," "okay," "next"), or otherwise positively reacting to the media. Negative feedback can also be based on attributes of the sensor data from the sensor(s) 230, such as the user frowning, crying, shaking their head (e.g., in a "no" motion), saying a negative statement (e.g., "no," "negative," "bad," "not this"), or otherwise negatively reacting to the virtual content.

In some examples, the feedback engine 260 provides the feedback to one or more ML systems of the imaging system 200 as training data to update the one or more trained ML model(s) 270 of the imaging system 200. For instance, the feedback engine 260 can provide the feedback as training data to the ML system(s) and/or the trained ML model(s) 270 to update the training for the second image processing engine 245, the first image processing engine 240, the gaze tracking engine 235, or a combination thereof. Positive feedback can be used to strengthen and/or reinforce weights associated with the outputs of the ML system(s) and/or the trained ML model(s) 270. Negative feedback can be used to weaken and/or remove weights associated with the outputs of the ML system(s) and/or the trained ML model(s) 270.

In some examples, certain elements of the imaging system 200 (e.g., the gaze tracking engine 235, the first image processing engine 240, the second image processing engine 245, the feedback engine 260, the trained ML model(s) 270, the user interactivity client application 280, and/or the user interactivity server application 285) include a software element, such as a set of instructions corresponding to a program, that is run on a processor such as the processor 810 of the computing system 800, the image processor 150, the host processor 152, the ISP 154, or a combination thereof. In some examples, these elements of the imaging system 200 include one or more hardware elements, such as a specialized processor (e.g., the processor 810 of the computing system 800, the image processor 150, the host processor 152, the ISP 154, or a combination thereof). In some examples, these elements of the imaging system 200 can include a combination of one or more software elements and one or more hardware elements.

In some examples, certain elements of the imaging system 200 (e.g., the gaze tracking engine 235, the first image processing engine 240, the second image processing engine 245, the feedback engine 260, the trained ML model(s) 270, the user interactivity client application 280, and/or the user interactivity server application 285) are run on different devices than those illustrated in FIG. 2. In some examples, the first image processing engine 240 can be located on, and/or run on, the user device 220 and/or the user device 210 instead of or in addition to the server(s) 205. In such examples, the server(s) 205 may be skipped and/or removed from the imaging system 200. In some examples, the second image processing engine 245 can be located on, and/or run on, the server(s) 205 and/or the user device 210 instead of or in addition to the user device 220. In such examples, the instance of the user interactivity client application 280 running on the user device 220 can send its arrangement 290 of representations of users to the server(s) 205 and/or the user device 210 before the second image processing engine 245 is able to generate the modified image data 247 (e.g., where the modified image data 247 is based on this arrangement 290). In some examples, the gaze tracking engine 235 can be located on, and/or run on, the user device 220 and/or the server(s) 205 instead of or in addition to the user device 210.

In some examples, certain elements of the user device 210 are also included in the user device 220. For instance, the user device 220 can also include sensor(s) like the sensor(s) 230, which can capture image data of the user 225 to be analyzed using an instance of the gaze tracking engine 235 on the user device 220 and processed using the first image processing engine 240 and/or an instance of the second image processing engine 245 on the user device 210 (e.g., based on the gaze information), with the resulting modified image data output using output device(s) 250 of the user device 210 and/or the transceiver(s) 255 of the user device 210 according to an arrangement 290 of representations of users determined by the instance of the user interactivity client application 280 on the user device 210.

While the instance of the user interactivity client application 280 on the user device 210 and the instance of the user interactivity client application 280 on the user device 220 are both illustrated as generating, including, and/or using the same arrangement 290 of representations of users, these two instances of the interactivity client application 280 may in some cases generate, include, and/or use different arrangements 290 relative to one another. For instance, the arrangement generated, includes, and/or used by the user interactivity client application 280 on the user device 210 may include a representation of the user 225 but not the user 215 (who is viewing the arrangement generated, includes, and/or used by the user interactivity client application 280 on the user device 210). On the other hand, the arrangement generated, includes, and/or used by the user interactivity client application 280 on the user device 220 may include a representation of the user 215 but not the user 225 (who is viewing the arrangement generated, includes, and/or used by the user interactivity client application 280 on the user device 220).

Figure 3A:
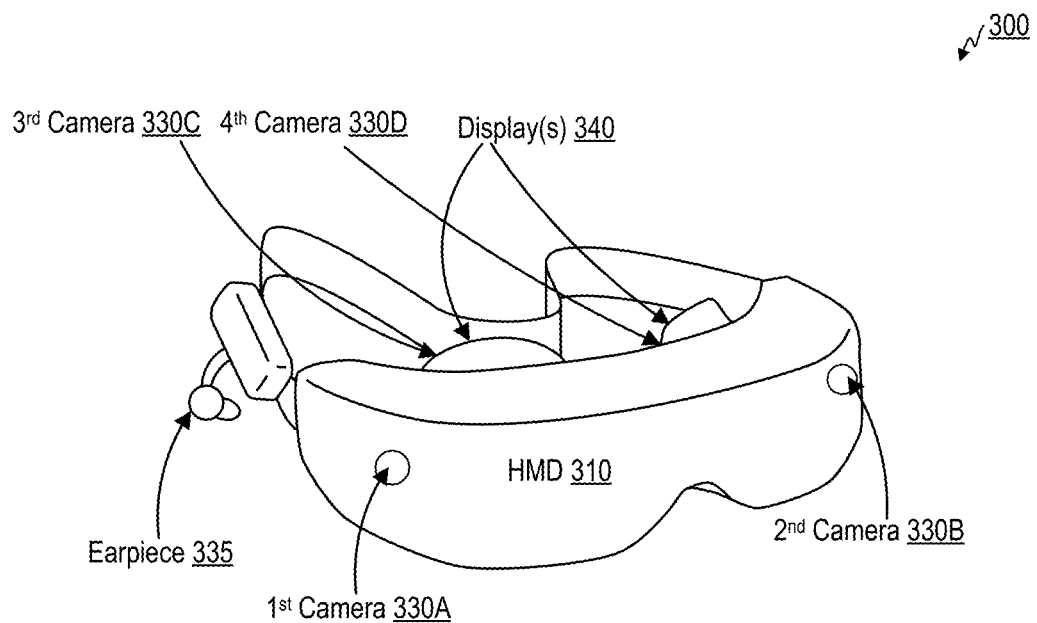
FIG. 3A is a perspective diagram illustrating a head-mounted display (HMD) that is used as an extended reality (XR) system, in accordance with some examples.

FIG. 3A is a perspective diagram 300 illustrating a head-mounted display (HMD) 310 that is used as an extended reality (XR) system 200. The HMD 310 may be, for example, an augmented reality (AR) headset, a virtual reality (VR) headset, a mixed reality (MR) headset, an extended reality (XR) headset, or some combination thereof. The HMD 310 may be an example of an imaging system 200. The HMD 310 includes a first camera 330A and a second camera 330B along a front portion of the HMD 310. The first camera 330A and the second camera 330B may be examples of the sensor(s) 230 of the imaging system 200. The HMD 310 includes a third camera 330C and a fourth camera 330D facing the eye(s) of the user as the eye(s) of the user face the display(s) 340. The third camera 330C and the fourth camera 330D may be examples of the sensor(s) 230 of the imaging system 200. In some examples, the HMD 310 may only have a single camera with a single image sensor. In some examples, the HMD 310 may include one or more additional cameras in addition to the first camera 330A, the second camera 330B, third camera 330C, and the fourth camera 330D. In some examples, the HMD 310 may include one or more additional sensors in addition to the first camera 330A, the second camera 330B, third camera 330C, and the fourth camera 330D, which may also include other types of sensor(s) 230 of the imaging system 200. In some examples, the first camera 330A, the second camera 330B, third camera 330C, and/or the fourth camera 330D may be examples of the image capture and processing system 100, the image capture device 105A, the image processing device 105B, or a combination thereof The HMD 310 may include one or more displays 340 that are visible to a user 320 wearing the HMD 310 on the user 320's head. The one or more displays 340 of the HMD 310 can be examples of the one or more displays of the output device(s) 250 of the imaging system 200. In some examples, the HMD 310 may include one display 340 and two viewfinders. The two viewfinders can include a left viewfinder for the user 320's left eye and a right viewfinder for the user 320's right eye. The left viewfinder can be oriented so that the left eye of the user 320 sees a left side of the display. The right viewfinder can be oriented so that the right eye of the user 320 sees a right side of the display. In some examples, the HMD 310 may include two displays 340, including a left display that displays content to the user 320's left eye and a right display that displays content to a user 320's right eye. The one or more displays 340 of the HMD 310 can be digital "pass-through" displays or optical "see-through" displays.

Figure 3B:
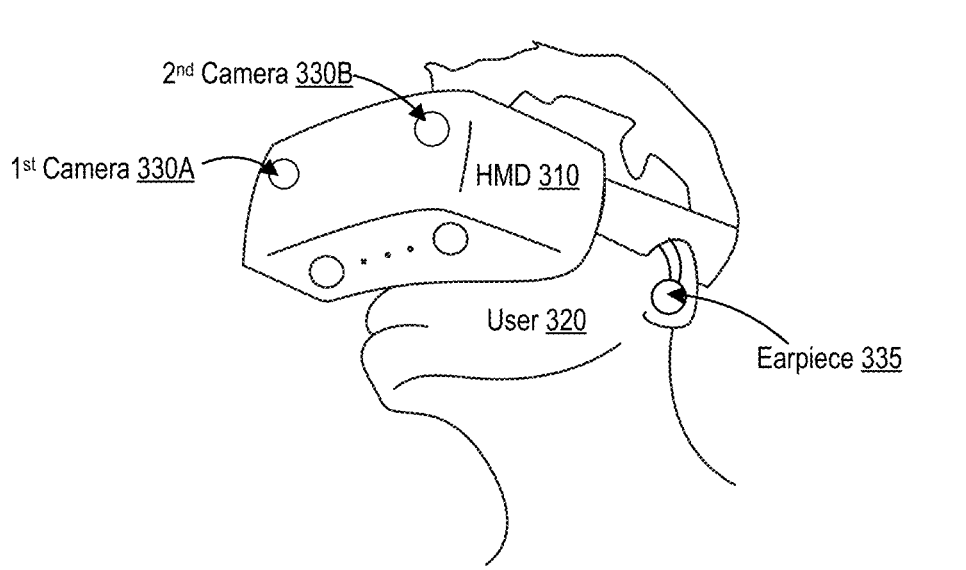
FIG. 3B is a perspective diagram illustrating the head-mounted display (HMD) of FIG. 3A being worn by a user, in accordance with some examples.

The HMD 310 may include one or more earpieces 335, which may function as speakers and/or headphones that output audio to one or more ears of a user of the HMD 310. One earpiece 335 is illustrated in FIGS. 3A and 3B, but it should be understood that the HMD 310 can include two earpieces, with one earpiece for each ear (left ear and right ear) of the user. In some examples, the HMD 310 can also include one or more microphones (not pictured). The one or more microphones can be examples of the sensor(s) 230 of the imaging system 200. In some examples, the audio output by the HMD 310 to the user through the one or more earpieces 335 may include, or be based on, audio recorded using the one or more microphones.

FIG. 3B is a perspective diagram 350 illustrating the head-mounted display (HMD) of FIG. 3A being worn by a user 320. The user 320 wears the HMD 310 on the user 320's head over the user 320's eyes. The HMD 310 can capture images with the first camera 330A and the second camera 330B. In some examples, the HMD 310 displays one or more output images toward the user 320's eyes using the display(s) 340. In some examples, the output images can include the image data 232, the modified image data 242, the modified image data 247, the modified image data 242 arranged according to the arrangement 290 of representations of users in the instance of the user interactivity client application 280 on the user device 220, the modified image data 247 arranged according to the arrangement 290 of representations of users in the instance of the user interactivity client application 280 on the user device 220, the input face image data 505, the front-facing face image data 510, the output face image data 515 for user A 535, the output face image data 520 for user B 540, the output face image data 525 for user C 545, or a combination thereof. The output images can be based on the images captured by the first camera 330A and the second camera 330B, for example with the virtual content overlaid. The output images may provide a stereoscopic view of the environment, in some cases with the virtual content overlaid and/or with other modifications. For example, the HMD 310 can display a first display image to the user 320's right eye, the first display image based on an image captured by the first camera 330A. The HMD 310 can display a second display image to the user 320's left eye, the second display image based on an image captured by the second camera 330B. For instance, the HMD 310 may provide overlaid virtual content in the display images overlaid over the images captured by the first camera 330A and the second camera 330B. The third camera 330C and the fourth camera 330D can capture images of the eyes of the before, during, and/or after the user views the display images displayed by the display(s) 340. This way, the sensor data from the third camera 330C and/or the fourth camera 330D can capture reactions to the virtual content by the user's eyes (and/or other portions of the user). An earpiece 335 of the HMD 310 is illustrated in an ear of the user 320. The HMD 310 may be outputting audio to the user 320 through the earpiece 335 and/or through another earpiece (not pictured) of the HMD 310 that is in the other ear (not pictured) of the user 320.

Figure 4A:
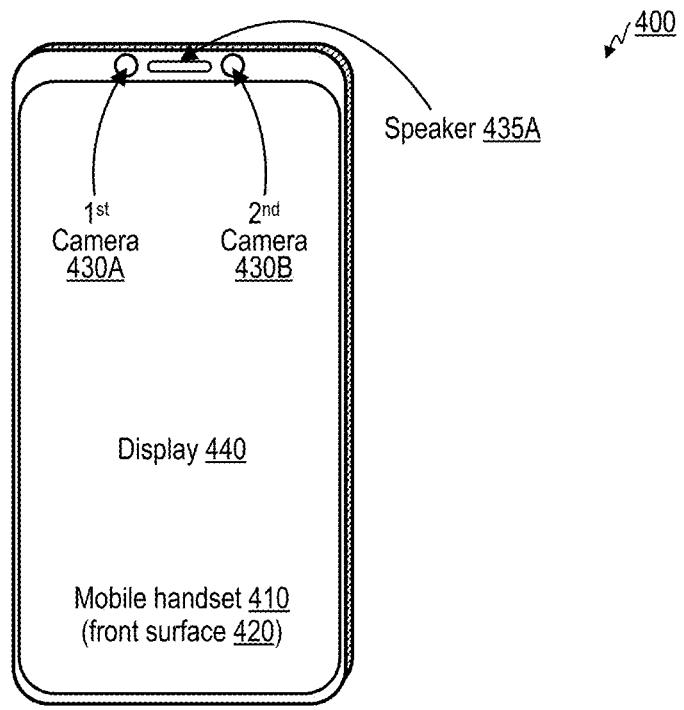
FIG. 4A is a perspective diagram illustrating a front surface of a mobile handset that includes front-facing cameras and that can be used as an extended reality (XR) system, in accordance with some examples.

FIG. 4A is a perspective diagram 400 illustrating a front surface of a mobile handset 410 that includes front-facing cameras and can be used as an extended reality (XR) system 200. The mobile handset 410 may be an example of an imaging system 200. The mobile handset 410 may be, for example, a cellular telephone, a satellite phone, a portable gaming console, a music player, a health tracking device, a wearable device, a wireless communication device, a laptop, a mobile device, any other type of computing device or computing system discussed herein, or a combination thereof The front surface 420 of the mobile handset 410 includes a display 440. The front surface 420 of the mobile handset 410 includes a first camera 430A and a second camera 430B. The first camera 430A and the second camera 430B may be examples of the sensor(s) 230 of the imaging system 200. The first camera 430A and the second camera 430B can face the user, including the eye(s) of the user, while content (e.g., the modified media output by the media modification engine 235) is displayed on the display 440. The display 440 may be an example of the display(s) of the output device(s) 250 of the imaging system 200.

The first camera 430A and the second camera 430B are illustrated in a bezel around the display 440 on the front surface 420 of the mobile handset 410. In some examples, the first camera 430A and the second camera 430B can be positioned in a notch or cutout that is cut out from the display 440 on the front surface 420 of the mobile handset 410. In some examples, the first camera 430A and the second camera 430B can be under-display cameras that are positioned between the display 440 and the rest of the mobile handset 410, so that light passes through a portion of the display 440 before reaching the first camera 430A and the second camera 430B. The first camera 430A and the second camera 430B of the perspective diagram 400 are front-facing cameras. The first camera 430A and the second camera 430B face a direction perpendicular to a planar surface of the front surface 420 of the mobile handset 410. The first camera 430A and the second camera 430B may be two of the one or more cameras of the mobile handset 410. In some examples, the front surface 420 of the mobile handset 410 may only have a single camera.

In some examples, the display 440 of the mobile handset 410 displays one or more output images toward the user using the mobile handset 410. In some examples, the output images can include the image data 232, the modified image data 242, the modified image data 247, the modified image data 242 arranged according to the arrangement 290 of representations of users in the instance of the user interactivity client application 280 on the user device 220, the modified image data 247 arranged according to the arrangement 290 of representations of users in the instance of the user interactivity client application 280 on the user device 220, the input face image data 505, the front-facing face image data 510, the output face image data 515 for user A 535, the output face image data 520 for user B 540, the output face image data 525 for user C 545, or a combination thereof. The output images can be based on the images captured by the first camera 430A, the second camera 430B, the third camera 430C, and/or the fourth camera 430D, for example with the virtual content overlaid.

In some examples, the front surface 420 of the mobile handset 410 may include one or more additional cameras in addition to the first camera 430A and the second camera 430B. The one or more additional cameras may also be examples of the sensor(s) 230 of the imaging system 200. In some examples, the front surface 420 of the mobile handset 410 may include one or more additional sensors in addition to the first camera 430A and the second camera 430B. The one or more additional sensors may also be examples of the sensor(s) 230 of the imaging system 200. In some cases, the front surface 420 of the mobile handset 410 includes more than one display 440. The one or more displays 440 of the front surface 420 of the mobile handset 410 can be examples of the display(s) of the output device(s) 250 of the imaging system 200. For example, the one or more displays 440 can include one or more touchscreen displays.

The mobile handset 410 may include one or more speakers 435A and/or other audio output devices (e.g., earphones or headphones or connectors thereto), which can output audio to one or more ears of a user of the mobile handset 410. One speaker 435A is illustrated in FIG. 4A, but it should be understood that the mobile handset 410 can include more than one speaker and/or other audio device. In some examples, the mobile handset 410 can also include one or more microphones (not pictured). The one or more microphones can be examples of the sensor(s) 230 of the imaging system 200. In some examples, the mobile handset 410 can include one or more microphones along and/or adjacent to the front surface 420 of the mobile handset 410, with these microphones being examples of the sensor(s) 230 of the imaging system 200. In some examples, the audio output by the mobile handset 410 to the user through the one or more speakers 435A and/or other audio output devices may include, or be based on, audio recorded using the one or more microphones.

Figure 4B:
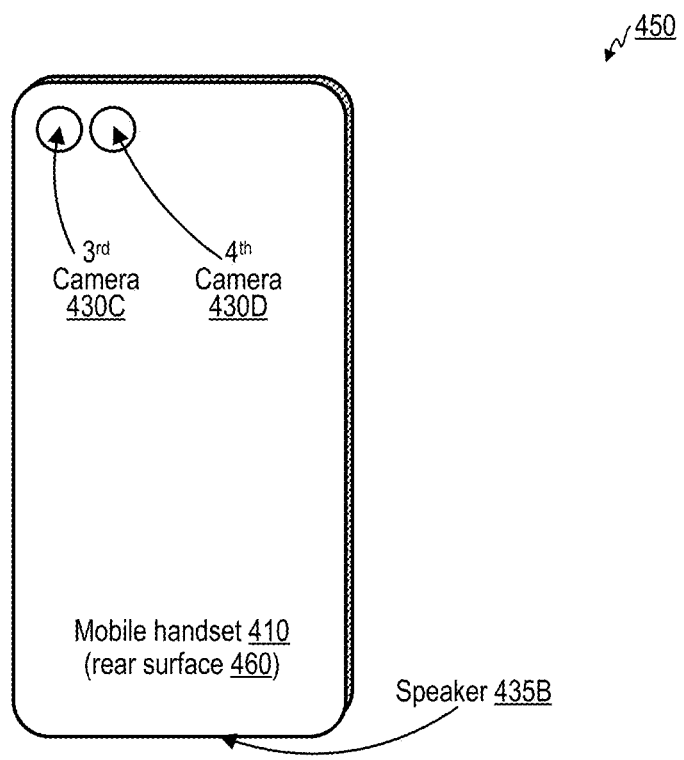
FIG. 4B is a perspective diagram illustrating a rear surface of a mobile handset that includes rear-facing cameras and that can be used as an extended reality (XR) system, in accordance with some examples.

FIG. 4B is a perspective diagram 450 illustrating a rear surface 460 of a mobile handset that includes rear-facing cameras and that can be used as an extended reality (XR) system 200. The mobile handset 410 includes a third camera 430C and a fourth camera 430D on the rear surface 460 of the mobile handset 410. The third camera 430C and the fourth camera 430D of the perspective diagram 450 are rear-facing. The third camera 430C and the fourth camera 430D may be examples of the sensor(s) 230 of the imaging system 200 of FIG. 2. The third camera 430C and the fourth camera 430D face a direction perpendicular to a planar surface of the rear surface 460 of the mobile handset 410.

The third camera 430C and the fourth camera 430D may be two of the one or more cameras of the mobile handset 410. In some examples, the rear surface 460 of the mobile handset 410 may only have a single camera. In some examples, the rear surface 460 of the mobile handset 410 may include one or more additional cameras in addition to the third camera 430C and the fourth camera 430D. The one or more additional cameras may also be examples of the sensor(s) 230 of the imaging system 200. In some examples, the rear surface 460 of the mobile handset 410 may include one or more additional sensors in addition to the third camera 430C and the fourth camera 430D. The one or more additional sensors may also be examples of the sensor(s) 230 of the imaging system 200. In some examples, the first camera 430A, the second camera 430B, third camera 430C, and/or the fourth camera 430D may be examples of the image capture and processing system 100, the image capture device 105A, the image processing device 105B, or a combination thereof The mobile handset 410 may include one or more speakers 435B and/or other audio output devices (e.g., earphones or headphones or connectors thereto), which can output audio to one or more ears of a user of the mobile handset 410. One speaker 435B is illustrated in FIG. 4B, but it should be understood that the mobile handset 410 can include more than one speaker and/or other audio device. In some examples, the mobile handset 410 can also include one or more microphones (not pictured). The one or more microphones can be examples of the sensor(s) 230 of the imaging system 200. In some examples, the mobile handset 410 can include one or more microphones along and/or adjacent to the rear surface 460 of the mobile handset 410, with these microphones being examples of the sensor(s) 230 of the imaging system 200. In some examples, the audio output by the mobile handset 410 to the user through the one or more speakers 435B and/or other audio output devices may include, or be based on, audio recorded using the one or more microphones.

The mobile handset 410 may use the display 440 on the front surface 420 as a pass-through display. For instance, the display 440 may display output images. The output images can be based on the images captured by the third camera 430C and/or the fourth camera 430D, for example with the virtual content overlaid and/or with modifications by the media modification engine 235 applied. The first camera 430A and/or the second camera 430B can capture images of the user's eyes (and/or other portions of the user) before, during, and/or after the display of the output images with the virtual content on the display 440. This way, the sensor data from the first camera 430A and/or the second camera 430B can capture reactions to the virtual content by the user's eyes (and/or other portions of the user).

Figure 5:
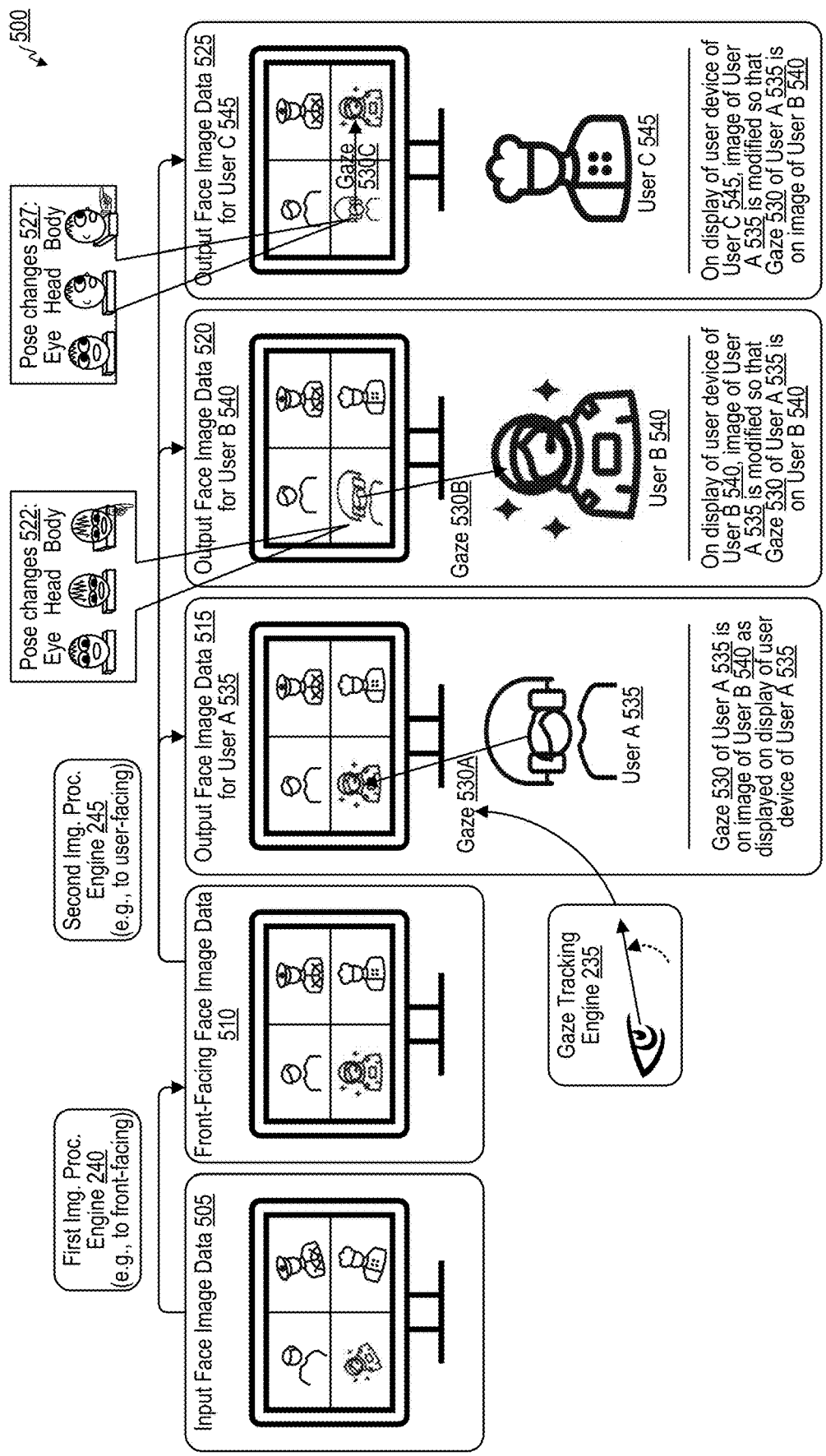
FIG. 5 is a block diagram illustrating a process for image processing for gaze alignment in a video conference, in accordance with some examples.

FIG. 5 is a block diagram illustrating a process 500 for image processing for gaze alignment in a video conference. In the process 500, input face image data 505 is illustrated that includes a grid of representations of users. Each representation of a user in the input face image data 505 is skewed and not necessarily looking at their respective camera. The input face image data 505, and/or the individual representations of users in the input face image data 505, represent examples of the image data 232 of FIG. 2.

In the process 500, the first image processing engine 240 processes the representations of the users in the input face image data 505 to generate the front-facing face image data 510. In each representation of a user in the front-facing face image data 510, the body, face, and/or eye(s) of the user appear to be facing forward (e.g., perpendicular to the display) regardless of where the body, face, and/or eye(s) of the user appeared to be facing in the input face image data 505.

In the process 500, the gaze tracking engine 235 identifies that the gaze 530A of user A 535 is directed toward an image representation of user B 540 that is displayed on a display of a user device of the user A 535. The user A 535 of FIG. 5 is an example of the user 215 of FIG. 2. The user device of the user A 535 is an example of the user device 210 of the user 215.

In the process 500, the second image processing engine 245 processes the representations of the users in the front-facing face image data 510 and/or in the input face image data 505 based on the gaze 530A identified by the gaze tracking engine 235 to generate the output face image data 515 for user A 535, the output face image data 520 for user B 540, and/or the output face image data 525 for user C 545. Since gaze information is not yet detected by the gaze tracking engine 235 for any other users other than user A 530A, the output face image data 515 for user A 535 appears to match the front-facing face image data 510. The user A 535 is a viewer of the output face image data 515 for user A 535.

Since the gaze 530A indicates that the user A 535 is looking at the image representation of user B 540, the image representation of the user A 535 in the output face image data 520 for user B 540 is processed so that the image representation of the user A 535 appears to be looking at the user B 540 as indicated by the gaze 530B in the output face image data 520 for user B 540. In particular, the image representation of the user A 535 appears to be looking down and slightly to the right at the user B 540 in the output face image data 520 for user B 540 (who is a viewer of the output face image data 520) as indicated by the diagonal arrow of the gaze 530B and the skew of the image representation of the user A 535 slightly downward and toward the right.

Since the gaze 530A indicates that the user A 535 is looking at the image representation of user B 540, the image representation of the user A 535 in the output face image data 525 for user C 545 is processed so that the image representation of the user A 535 appears to be looking at the image representation of the user B 540 as indicated by the gaze 530C in the output face image data 525 for user B 540. In particular, the image representation of the user A 535 appears to be looking to the right at the image representation of the user B 540 on the display of user C 545 in the output face image data 525 for user C 545 as indicated by the right-facing arrow of the gaze 530C and the skew of the image representation of the user A 535 toward the right. The user C 545 is a viewer of the output face image data 525 for user C 545.

The image representations of the user A 535 in the output face image data 520 for user B 540 and/or the output face image data 525 for user C 545 can be modified by the second image processing engine 245 so that the body, face, and/or eye(s) of the user A 535 appear to be facing the user B 540, or the image representation of the user B 540, regardless of where the body, face, and/or eye(s) of the user appeared to be facing in the input face image data 505 and/or in the front-facing face image data 510.

The modifications to the output face image data 520 for user B 540 to depict the gaze 530B toward the viewing user B 540 can include changes to eye pose, head/face pose, and/or body pose of the users in the arrangement, for example as illustrated in the pose changes 522. Similarly, the modifications to the output face image data 525 for user C 545 to depict the gaze 530C toward the depiction of the user B 540 can include changes to eye pose, head/face pose, and/or body pose of the users in the arrangement, for example as illustrated in the pose changes 527. For instance, for the pose changes 522, the eyes are directed forward and slightly downward (e.g., based on the direction of the gaze 530B) for the eye pose change, the head are directed forward and slightly downward (e.g., based on the direction of the gaze 530B) for the head pose change, and the shoulders and torso are directed forward and slightly downward (e.g., based on the direction of the gaze 530B) and the hand and finger are pointing slightly downwards (e.g., based on the direction of the gaze 530B) for the body pose change. Similarly, for the pose changes 527, the eyes are directed to the right (e.g., based on the direction of the gaze 530C) for the eye pose change, the head are directed slightly to the right (e.g., based on the direction of the gaze 530C) for the head pose change, and the shoulders and torso are directed slightly to the right (e.g., based on the direction of the gaze 530C) and the hand and finger are pointing to the right (e.g., based on the direction of the gaze 530C) for the body pose change.

Figure 6:
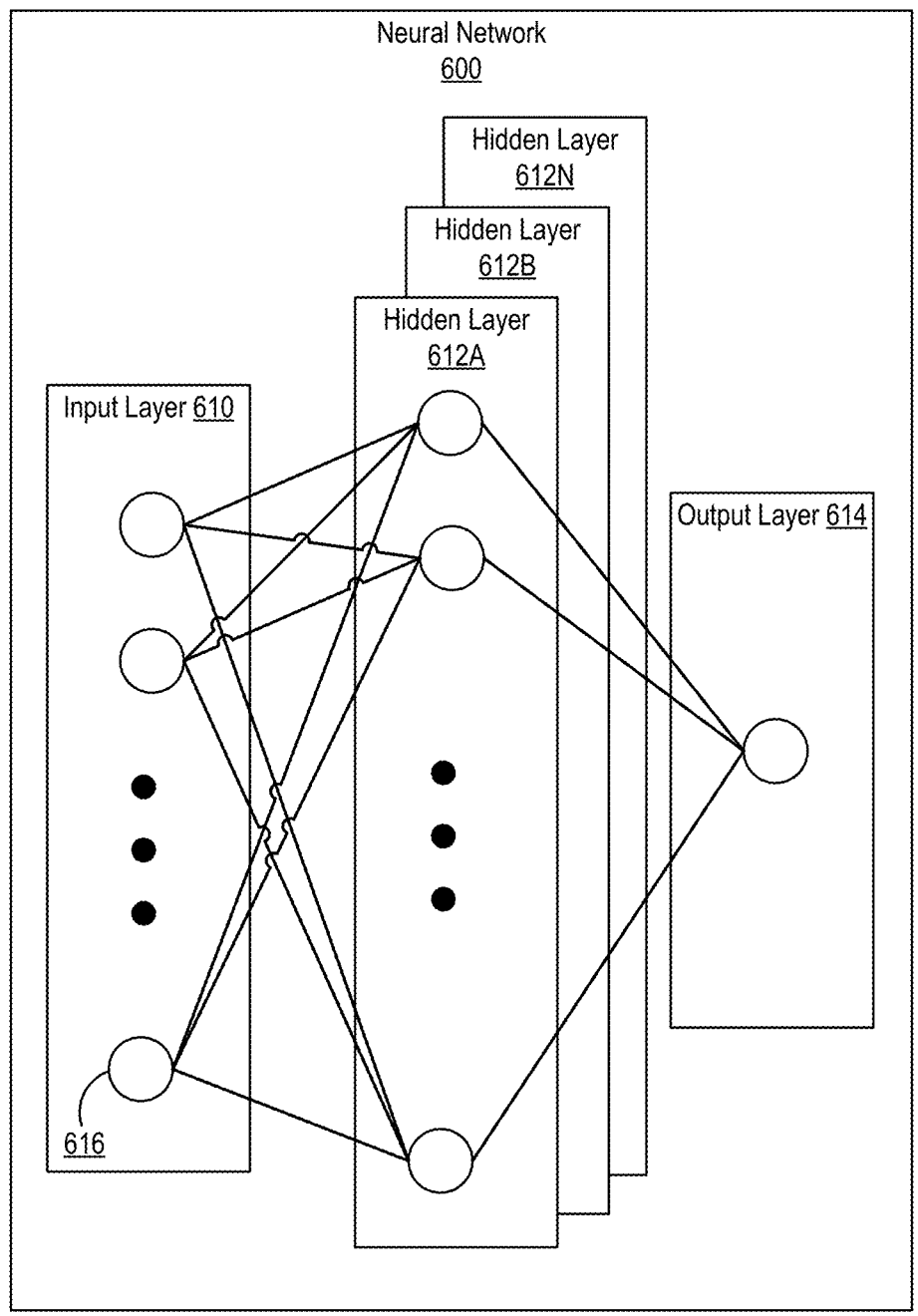
FIG. 6 is a block diagram illustrating an example of a neural network that can be used for image processing operations, in accordance with some examples.

FIG. 6 is a block diagram illustrating an example of a neural network (NN) 600 that can be used for media processing operations. The neural network 600 can include any type of deep network, such as a convolutional neural network (CNN), an autoencoder, a deep belief net (DBN), a Recurrent Neural Network (RNN), a Generative Adversarial Networks (GAN), and/or other type of neural network. The neural network 600 may be an example of one of the one or more trained machine learning models 270 of the imaging system 200, which may be used by the gaze tracking engine 235, the first image processing engine 240, the second image processing engine 245, or a combination thereof.

An input layer 610 of the neural network 600 includes input data. The input data of the input layer 610 can include data representing the pixels of one or more input image frames. In some examples, the input data of the input layer 610 includes data representing the pixels of image data (e.g., image data 232 captured by the sensor(s) 230, image(s) captured by the third camera 330C, image(s) captured by the fourth camera 330D, image(s) captured by the first camera 430A, image(s) captured by the second camera 430B, the input face image data 505, the front-facing face image data 510, the image data of operation 705) and/or metadata corresponding to the image data. In some examples, the input data of the input layer 610 includes gaze information from the gaze tracking engine 235, information about the arrangement of representations of users in the instance of the user interactivity client application 280 on the user device 210 (e.g., arrangement 290), information about the arrangement of representations of users in the instance of the user interactivity client application 280 on the user device 220 (e.g., arrangement 290), or a combination thereof.

The images can include image data from an image sensor including raw pixel data (including a single color per pixel based, for example, on a Bayer filter) or processed pixel values (e.g., RGB pixels of an RGB image). The neural network 600 includes multiple hidden layers 612A, 612B, through 612N. The hidden layers 612A, 612B, through 612N include "N" number of hidden layers, where "N" is an integer greater than or equal to one. The number of hidden layers can be made to include as many layers as needed for the given application. The neural network 600 further includes an output layer 614 that provides an output resulting from the processing performed by the hidden layers 612A, 612B, through 612N.

In some examples, the output layer 614 can provide an output image, such as the modified image data 242, the modified image data 247, the modified image data 242 arranged according to the arrangement of representations of users in the instance of the user interactivity client application 280 on the user device 220, the modified image data 247 arranged according to the arrangement of representations of users in the instance of the user interactivity client application 280 on the user device 220, the front-facing face image data 510, the output face image data 515 for user A 535, the output face image data 520 for user B 540, the output face image data 525 for user C 545, and/or the modified image data of operations 720-725. In some examples, the output layer 614 can provide other types of data as well, such as the gaze information from the gaze tracking engine 235.

The neural network 600 is a multi-layer neural network of interconnected filters. Each filter can be trained to learn a feature representative of the input data. Information associated with the filters is shared among the different layers and each layer retains information as information is processed. In some cases, the neural network 600 can include a feed-forward network, in which case there are no feedback connections where outputs of the network are fed back into itself. In some cases, the network 600 can include a recurrent neural network, which can have loops that allow information to be carried across nodes while reading in input.

In some cases, information can be exchanged between the layers through node-to-node interconnections between the various layers. In some cases, the network can include a convolutional neural network, which may not link every node in one layer to every other node in the next layer. In networks where information is exchanged between layers, nodes of the input layer 610 can activate a set of nodes in the first hidden layer 612A. For example, as shown, each of the input nodes of the input layer 610 can be connected to each of the nodes of the first hidden layer 612A. The nodes of a hidden layer can transform the information of each input node by applying activation functions (e.g., filters) to this information. The information derived from the transformation can then be passed to and can activate the nodes of the next hidden layer 612B, which can perform their own designated functions. Example functions include convolutional functions, downscaling, upscaling, data transformation, and/or any other suitable functions. The output of the hidden layer 612B can then activate nodes of the next hidden layer, and so on. The output of the last hidden layer 612N can activate one or more nodes of the output layer 614, which provides a processed output image. In some cases, while nodes (e.g., node 616) in the neural network 600 are shown as having multiple output lines, a node has a single output and all lines shown as being output from a node represent the same output value.

In some cases, each node or interconnection between nodes can have a weight that is a set of parameters derived from the training of the neural network 600. For example, an interconnection between nodes can represent a piece of information learned about the interconnected nodes. The interconnection can have a tunable numeric weight that can be tuned (e.g., based on a training dataset), allowing the neural network 600 to be adaptive to inputs and able to learn as more and more data is processed.

The neural network 600 is pre-trained to process the features from the data in the input layer 610 using the different hidden layers 612A, 612B, through 612N in order to provide the output through the output layer 614.

Figure 7:
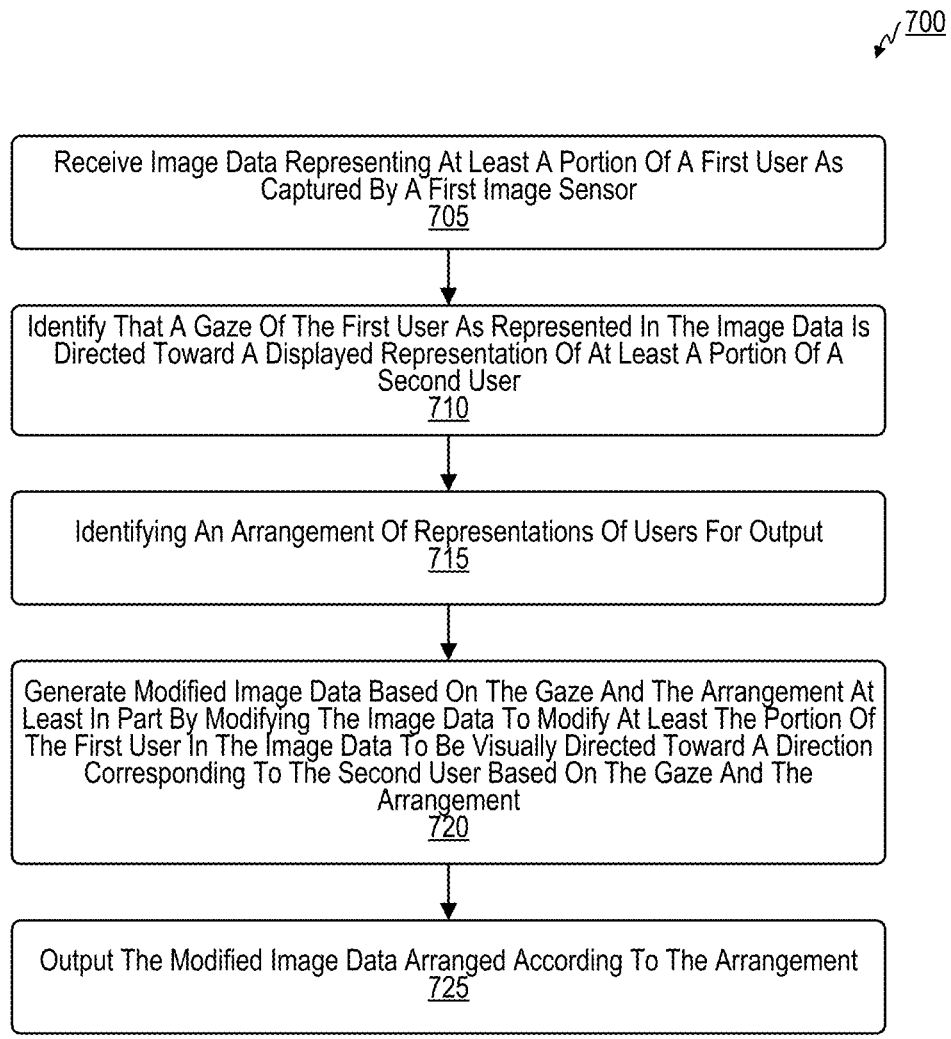
FIG. 7 is a flow diagram illustrating an imaging process, in accordance with some examples.

FIG. 7 is a flow diagram illustrating an imaging process 700. The imaging process 700 may be performed by an imaging system. In some examples, the imaging system can include, for example, the image capture and processing system 100, the image capture device 105A, the image processing device 105B, the image processor 150, the ISP 154, the host processor 152, the imaging system 200, the server(s) 205, the user device 210, the user device 220, the HMD 310, the mobile handset 410, the imaging system of FIG. 5, neural network 600, the computing system 800, the processor 810, or a combination thereof.

At operation 705, the imaging system is configured to, and can, receive image data representing at least a portion of a first user as captured by a first image sensor. In some examples, the imaging system includes an image sensor connector that coupled and/or connects the image sensor to a remainder of the imaging system (e.g., including the processor and/or the memory of the imaging system), In some examples, the imaging system receives the image data from the image sensor by receiving the image data from, over, and/or using the image sensor connector.

Examples of the image sensor includes the image sensor 130, the sensor(s) 230, the first camera 330A, the second camera 330B, the third camera 330C, the fourth camera 330D, the first camera 430A, the second camera 430B, the third camera 430C, the fourth camera 430D, an image sensor that captures the input image data 505, an image sensor used to capture an image used as input data for the input layer 610 of the NN 600, the input device 845, another image sensor described herein, another sensor described herein, or a combination thereof.

Examples of the image data include image data captured using the image capture and processing system 100, image data captured using image sensor(s) of the sensor(s) 230, image data captured using the first camera 330A, image data captured using the second camera 330B, image data captured using the third camera 330C, image data captured using the fourth camera 330D, image data captured using the first camera 430A, image data captured using the second camera 430B, image data captured using the third camera 430C, image data captured using the fourth camera 430D, an image used as input data for the input layer 610 of the NN 600, an image captured using the input device 845, another image described herein, another set of image data described herein, or a combination thereof.

At operation 710, the imaging system is configured to, and can, identify that a gaze of the first user as represented in the image data is directed toward a displayed representation of at least a portion of a second user. In some examples, the imaging system is configured to, and can, determine, based on the image data, that the gaze of the first user is directed toward a first gaze area that includes a displayed representation of a face of a second user. Examples of the gaze determined in the image data include the gaze of the user 215 on display(s) of the user device 210 as determined by the gaze tracking engine 235 based on the sensor(s) 230, a gaze of the user 320 on the display(s) 340 as determined based on the third camera 330C and/or the fourth camera 330D, the gaze of a user of the mobile handset 410 on the display 440 of the mobile handset 410 as determined based on the first camera 430A and/or the second camera 430B, the gaze 530A of the user A 535 on the output face image data 515, or a combination thereof.

In some examples, identifying that the gaze of the first user as represented in the image data is directed toward the displayed representation of at least the portion of the second user as in operation 710 includes analyzing the image data in comparison to a known position of the displayed representation of at least the portion of the second user, for example as performed by the gaze tracking engine 235. In some examples, identifying that the gaze of the first user as represented in the image data is directed toward the displayed representation of at least the portion of the second user as in operation 710 includes receiving gaze information identifying that the gaze of the first user as represented in the image data is directed toward the displayed representation of at least the portion of the second user. For instance as the server(s) 205 and/or user device 220 can receive such gaze information from the gaze tracking engine 235 of the user device 210.

At operation 715, the imaging system is configured to, and can, identify an arrangement of representations of users for output. Examples of the arrangement include the arrangement 290 as well as the grids illustrated in FIG. 5 in the input face image data 505, in the front-facing face image data 510, in the output face image data 515 for user A 535, in the output face image data 520 for user B 540, and in the output face image data 525 for user C 545.

At operation 720, the imaging system is configured to, and can, generate modified image data based on the gaze and the arrangement at least in part by modifying the image data to modify at least the portion of the first user in the image data to be visually directed toward a direction corresponding to the second user based on the gaze and the arrangement. Examples of the modified image data include the modified image data 242, the modified image data 247, the front-facing face image data 510, the output face image data 515 for user A 535, the output face image data 520 for user B 540, the output face image data 525 for user C 545, image data output via the output layer 614 of the NN 600, or a combination thereof. In some examples, the modification(s) of operation 720 are performed using the image processing device 105B, the image processor 150, the ISP 154, the host processor 152, the imaging system 200, the server(s) 205, the user device 210, the user device 220, the first image processing engine 240, the second image processing engine 245, the trained ML model(s) 270, the HMD 310, the mobile handset 410, the imaging system of FIG. 5, neural network 600, the computing system 800, the processor 810, or a combination thereof.

In some examples, modifying at least the portion of the first user in the image data to be visually directed toward the direction corresponding to the second user includes modifying at least one of an eye pose of one or both eyes of the first user in the image data to be visually directed toward the direction corresponding to the second user, modifying a head pose of at least part of a head of the first user in the image data to be visually directed toward the direction corresponding to the second user, modifying a body pose of at least part of a body of the first user in the image data to be visually directed toward the direction corresponding to the second user. The modification(s) to the eye pose can include modification(s) of the representation(s) of the eye(s) of the user from the image data to the modified image data to turn and/or move the irise(s) and/or pupil(s) of the eye(s) to be visually directed toward the direction corresponding to the second user. The modification(s) to the head pose can include modification(s) of the representation(s) of at least a portion of the face, eyes, nose, mouth, ears, forehead, chin, cheeks, and/or other portions of the head of the user from the image data to the modified image data to turn and/or move these head features so that the face is visually directed toward the direction corresponding to the second user. The modification(s) to the body pose can include modification(s) of the representation(s) of at least a portion of the body of the user (e.g., eye(s), face, head, neck, shoulders, torso, arm(s), leg(s), finger(s), foot/feet, toe(s), or combinations thereof) from the image data to the modified image data to turn and/or move at least the portion of the body to be visually directed toward the direction corresponding to the second user. The modification(s) to the eye pose, head pose, and/or body pose may include modifications to visually pose at least a portion of the user into making one or more gestures, for instance to use the hand(s) and/or finger(s) of the user toward the direction corresponding to the second user.

Examples of changes to eye pose, head pose, and body pose are illustrated in the pose changes 522 and the pose changes 527 of FIG. 5. For instance, for the pose changes 522, the eyes are directed forward and slightly downward (e.g., based on the direction of the gaze 530B) for the eye pose change, the head are directed forward and slightly downward (e.g., based on the direction of the gaze 530B) for the head pose change, and the shoulders and torso are directed forward and slightly downward (e.g., based on the direction of the gaze 530B) and the hand and finger are pointing slightly downwards (e.g., based on the direction of the gaze 530B) for the body pose change. For the pose changes 527, the eyes are directed to the right (e.g., based on the direction of the gaze 530C) for the eye pose change, the head are directed slightly to the right (e.g., based on the direction of the gaze 530C) for the head pose change, and the shoulders and torso are directed slightly to the right (e.g., based on the direction of the gaze 530C) and the hand and finger are pointing to the right (e.g., based on the direction of the gaze 530C) for the body pose change.

In some examples, generating the modified image data includes using one or more trained machine learning models to generate the modified image data at least in part by providing the image data and the gaze and the arrangement as inputs to the one or more trained machine learning models. Examples of the one or more trained machine learning models include the one or more trained ML model(s) 270 and the NN 600. In some examples, the one or more trained machine learning models include one or more NNs (e.g., NN 600), one or more CNNs) one or more TDNNs, one or more deep networks, one or more autoencoders, one or more DBNs, one or more RNNs, one or more GANs, one or more cGANs, one or more other types of NNs, one or more trained SVMs, one or more trained RFs, one or more computer vision systems, one or more deep learning systems, or combinations thereof. In an illustrative example, the one or more trained machine learning models include a GAN and/or a cGAN.

In some examples, generating the modified image data as in operation 720 includes generating intermediate image data at least in part by modifying the image data to modify at least the portion of the first user in the image data to be visually directed toward a forward direction. The forward direction may be perpendicular to an image plane of the intermediate image data, the arrangement, a display on which the intermediate image data may be displayed, or a combination thereof. In such examples, generating the modified image data as in operation 720 also includes generating the modified image data at least in part by modifying the intermediate image data to modify at least the portion of the first user in the intermediate image data to be visually directed toward the direction corresponding to the second user. Examples of the intermediate image data include the modified image data 242 and the front-facing face image data 510 of FIG. 5. The intermediate image data may be generated to normalize the image data into a standard format before modifying the image data further to be directed toward the direction corresponding to the second user. In some examples, generating the intermediate image data includes using one or more trained machine learning models to generate the modified image data at least in part by providing the image data and/or the arrangement as input(s) to the one or more trained machine learning models. In some examples, the one or more trained machine learning models include one or more NNs (e.g., NN 600), one or more CNNs) one or more TDNNs, one or more deep networks, one or more autoencoders, one or more DBNs, one or more RNNs, one or more GANs, one or more cGANs, one or more other types of NNs, one or more trained SVMs, one or more trained RFs, one or more computer vision systems, one or more deep learning systems, or combinations thereof.

In some examples, the imaging system is configured to, and can, receive prior image data representing at least the portion of the first user and a second portion of the first use. The prior image data is captured by the first image sensor before capture of the image data by the first image sensor. In some examples the generation of the modified image data by the imaging system can include incorporating at least some of the prior image data that represents the second portion of the first user into the modified image data. For instance, if the modification(s) to the image data that produce the modified image data include a change to head pose that turns the user's head to one side from a relatively front-facing pose, the image data may lack information identifying how the side(s) of the user's head look. The imaging system can retrieve prior image data where the user's head was turned more to the side, may use this prior image data to identify how the side(s) of the user's head look, and may use this information about how the side(s) of the user's head look to generate the modified image data in which the user is depicted with his/her head turned to the side.

In some examples, generating the modified image data as in operation 720 includes modifying the image data to modify at least the portion of the first user from a realistic form into an avatar form. The realistic form may be a photographic form as captured by a camera and/or image sensor, optionally with image processing applied. The avatar form may, for instance, be a cartoon form, which may in some cases be 2 D, 3 D, stationary, or animated. The use of the avatar form can protect the user's privacy, since the user's real face is not shown. In some examples, the first user has a facial expression as represented in the image data, and generating the modified image data as in operation 720 includes modifying the avatar form to apply an indicator of the facial expression to the avatar form. For instance, if the user is smiling or laughing in the image data, a smile or laughing animation can be applied to the avatar corresponding to the user. If the user is frowning or crying in the image data, a frown or a crying animation can be applied to the avatar corresponding to the user. If the user is moving his/her mouth to speak in the image data, corresponding mouth motions can be applied to the avatar corresponding to the user, so that the avatar appears to be moving his/her mouth to speak the same words as the user.

In some examples, the first user has a facial expression as represented in the image data. In some examples, generating the modified image data in operation 720 includes modifying the image data to modify at least the portion of the first user to mask the facial expression. Masking the user's facial expression can protect the user's privacy, since the user's real facial expressions are not shown. For instance, regardless of whether the user is smiling, laughing, frowning, crying, or any other facial expression, the user can appear to have a neutral facial expression, or a facial expression of choice, applied. The facial expression can be chosen by the user, for instance, using a user interface, allowing the user to select when he/she appears to be smiling, laughing, frowning, crying, or performing any other facial expression, regardless of the user's real facial expression. The facial expression can be chosen intelligently by the imaging system, for instance to appear to smile or laugh when something positive was said by one of the users, to appear to smile or laugh when other users are smiling or laughing, to appear to frown or cry when something negative was said by one of the users, to appear to frown or cry when other users are frowning or crying, and the like.

At operation 725, the imaging system is configured to, and can, output the modified image data arranged according to the arrangement. In some examples, the imaging system includes a display, and outputting the modified image data arranged according to the arrangement includes displaying the modified image data using the display. Examples of the display include the output device(s) 250, the display(s) 340 of the HMD 310, the display 440 of the mobile handset 410, the displays illustrated in FIG. 5, the output device 835, or a combination thereof.

In some examples, the imaging system includes a communication interface, and outputting the modified image data arranged according to the arrangement includes sending the modified image data to a recipient device using the communication interface. The recipient device renders the modified image data arranged according to the arrangement for display using a display (e.g., a display of the recipient device). The recipient device displays the modified image data arranged according to the arrangement using the display. Examples of the communication interface include the transceiver(s) 255, a communication interface of the server(s) 205, a communication interface of the user device 210, the output device 835, the communication interface 840, or a combination thereof. Examples of the recipient device include the image capture and processing system 100, the image capture device 105A, the image processing device 105B, the image processor 150, the ISP 154, the host processor 152, the imaging system 200, the server(s) 205, the user device 210, the user device 220, the HMD 310, the mobile handset 410, the imaging system of FIG. 5, neural network 600, the computing system 800, the processor 810, or a combination thereof.

In some examples, the arrangement of representations of users includes the modified image data and second image data representing at least the portion of the second user. In such examples, the direction corresponding to the second user is a direction from a position of the modified image data in the arrangement to a position of the second image data in the arrangement. In such examples, at least a component of the direction corresponding to the second user is parallel to an image plane of the arrangement. An illustrative example is illustrated in FIG. 5 as the output face image data 525 for User C 545. In the output face image data 525, a modified representation of the User A 535 appears in the lower-left corner of the arrangement (grid) displayed on the display, and represents the modified image data. In the output face image data 525, a representation of the User B 540 appears in the lower-right corner of the arrangement (grid) displayed on the display, and represents the second image data. In the output face image data 525, the direction corresponding to the second user is the direction of the gaze 530C, from the modified image data (e.g., from the modified representation of the User A 535 in the lower-left corner of the arrangement) to the second image data (e.g., to the representation of the User B 540 appears in the lower-right corner of the arrangement). Hence, the modified image data (e.g., the modified representation of the User A 535 in the lower-left corner of the arrangement) appears to be directed to the right, in the direction of the gaze 530C. The direction corresponding to the second user can be represented as a vector, such as the right-facing arrow representing the gaze 530C in the output face image data 525. The vector may be purely parallel to the image plane of the display, the arrangement, the modified image data, and/or the second image data. The vector may in some cases be diagonal with respect to this image plane, and may thus include a vector component that is parallel to this image plane and a vector component that is perpendicular to this image plane. For instance, the modified image data can be modified so that at least the portion of the user appears to be directed at a diagonal angle, partially directed toward the second user data and partially directed toward the viewer (e.g., the viewer being User C 545 in the example of the output face image data 525). Thus, at least a component of the direction corresponding to the second user is parallel to an image plane of the display, the arrangement, the modified image data, and/or the second image data.

In some examples, the second user is a viewer of the modified image data as output according to the arrangement. In such examples, the direction corresponding to the second user is a direction toward the viewer. In such examples, at least a component of the direction corresponding to the second user is perpendicular to an image plane of the arrangement. An illustrative example is illustrated in FIG. 5 as the output face image data 520 for User B 540. In the output face image data 520, a modified representation of the User A 535 appears in the lower-left corner of the arrangement (grid) displayed on the display, and represents the modified image data. With respect to the output face image data 520, the User B 540 is the viewer of the output face image data 520. With respect to the output face image data 520, the direction corresponding to the second user is the direction of the gaze 530B, from the modified image data (e.g., from the modified representation of the User A 535 in the lower-left corner of the arrangement) to the viewer (e.g., to the user B 540 viewing the output face image data 520). Hence, the modified image data (e.g., the modified representation of the User A 535 in the lower-left corner of the arrangement) appears to be directed forward and slightly down, in the direction of the gaze 530B. The direction corresponding to the second user can be represented as a vector, such as the forward-and-down-facing arrow representing the gaze 530B with respect to the output face image data 520. The vector may be purely perpendicular to the image plane of the display, the arrangement, the modified image data, and/or the second image data. The vector may in some cases be diagonal with respect to this image plane, and may thus include a vector component that is perpendicular to this image plane and a vector component that is parallel to this image plane. For instance, if the viewer (e.g., the user B 540) is standing off to one side of the display, camera(s) of the user device of the user B 540 can detect this, and the modified image data can be modified so that at least the portion of the user appears to be looking off to that same side to look at the viewer (e.g., at the user B 540). The modified image data can be modified in real-time as the viewer (e.g., at the user B 540) moved about their environment so that the at least the portion of the user appears to be "following" the viewer (e.g., at the user B 540) as the viewer (e.g., at the user B 540) moves about their environment. Thus, at least a component of the direction corresponding to the second user is parallel to an image plane of the display, the arrangement, the modified image data, and/or the second image data.

In some examples, the imaging system is configured to, and can, receive second image data representing at least a portion of the second user as captured by a second image sensor, for instance as discussed above with respect to the receipt of image data of operation 705. In some examples, the imaging system is configured to, and can, identify that a second gaze of the second user as represented in the second image data is directed toward a second gaze area, for instance as discussed above with respect to the identification of the gaze of operation 710. The imaging system can generate modified second image data based on the second gaze and the arrangement at least in part by modifying the second image data to modify at least the portion of the second user in the second image data to be visually directed toward a direction corresponding to the second gaze area based on the second gaze and the arrangement, for instance as discussed above with respect to the generation of the modified image data of operation 720. The imaging system can output the modified second image data arranged according to the arrangement, for instance as discussed above with respect to the outputting of the modified image data of operation 725.

In some examples, generating the modified second image data includes using one or more trained machine learning models to generate the modified second image data at least in part by providing the second image data and the second gaze and the arrangement as inputs to the one or more trained machine learning models. Examples of the one or more trained machine learning models include the one or more trained ML model(s) 270 and the NN 600. In some examples, the one or more trained machine learning models include one or more NNs (e.g., NN 600), one or more CNNs) one or more TDNNs, one or more deep networks, one or more autoencoders, one or more DBNs, one or more RNNs, one or more GANs, one or more cGANs, one or more other types of NNs, one or more trained SVMs, one or more trained RFs, one or more computer vision systems, one or more deep learning systems, or combinations thereof In an illustrative example, the one or more trained machine learning models include a GAN and/or a cGAN.

In some examples, the second gaze area includes a displayed representation of at least the portion of the first user. In such examples, the direction corresponding to the second gaze area is a direction from a position of the modified second image data in the arrangement to a position of the modified image data in the arrangement, for instance as in the gaze 530C of the output face image data 525 of FIG. 5. In such examples, at least a component of the direction corresponding to the second gaze area is parallel to an image plane of the arrangement, for instance as in the gaze 530C of the output face image data 525 of FIG. 5.

In some examples, the second gaze area includes a displayed representation of at least a portion of a third user. In such examples, the direction corresponding to the second gaze area is a direction from a position of the modified second image data in the arrangement to a position of third image data representing the third user in the arrangement, for instance as in the gaze 530C of the output face image data 525 of FIG. 5. In such examples, at least a component of the direction corresponding to the second gaze area is parallel to an image plane of the arrangement, for instance as in the gaze 530C of the output face image data 525 of FIG. 5.

In some examples, the imaging system can includes: means for receiving image data representing at least a portion of a first user as captured by a first image sensor; means for identifying that a gaze of the first user as represented in the image data is directed toward a displayed representation of at least a portion of a second user; means for identifying an arrangement of representations of users for output; means for generating modified image data based on the gaze and the arrangement at least in part by modifying the image data to modify at least the portion of the first user in the image data to be visually directed toward a direction corresponding to the second user based on the gaze and the arrangement; and means for outputting the modified image data arranged according to the arrangement.

In some examples, the means for receiving the image data includes the image capture and processing system 100, the image capture device 105A, the image processing device 105B, the image processor 150, the ISP 154, the host processor 152, the image sensor 130, the sensor(s) 230, the first camera 330A, the second camera 330B, the third camera 330C, the fourth camera 330D, the first camera 430A, the second camera 430B, the third camera 430C, the fourth camera 430D, an image sensor that captures the input image data 505, an image sensor used to capture an image used as input data for the input layer 610 of the NN 600, the input device 845, another image sensor described herein, another sensor described herein, or a combination thereof.

In some examples, the means for identifying that the gaze of the first user is directed toward a displayed representation of at least a portion of a second user includes the image capture and processing system 100, the image processing device 105B, the image processor 150, the ISP 154, the host processor 152, the imaging system 200, the server(s) 205, the user device 210, the user device 220, the gaze tracking engine 235, the trained ML model(s) 270, the HMD 310, the mobile handset 410, the imaging system of FIG. 5, neural network 600, the computing system 800, the processor 810, or a combination thereof.

In some examples, the means for identifying the arrangement of representations of users for output includes the image capture and processing system 100, the image processing device 105B, the image processor 150, the ISP 154, the host processor 152, the imaging system 200, the server(s) 205, the user device 210, the user device 220, the user interactivity client application 280 (an instance on the user device 210 and/or an instance on the user device 220), the user interactivity server application 285, the trained ML model(s) 270, the HMD 310, the mobile handset 410, the imaging system of FIG. 5, neural network 600, the computing system 800, the processor 810, or a combination thereof In some examples, the means for generating the modified image data includes the image capture and processing system 100, the image processing device 105B, the image processor 150, the ISP 154, the host processor 152, the imaging system 200, the server(s) 205, the user device 210, the user device 220, the first image processing engine 240, the second image processing engine 245, the trained ML model(s) 270, the HMD 310, the mobile handset 410, the imaging system of FIG. 5, neural network 600, the computing system 800, the processor 810, or a combination thereof In some examples, the means for outputting the modified image data arranged according to the arrangement includes the I/O 156, the I/O 160, the output device(s) 250, the transceiver(s) 255, the display(s) 340, the display 440, the display(s) of FIG. 5, the output device 835, the communication interface 840, or a combination thereof In some examples, the processes described herein (e.g., the process of FIG. 1, the process of FIG. 2, the process 500 of FIG. 5, the process of FIG. 6, the process 700 of FIG. 7, and/or other processes described herein) may be performed by a computing device or apparatus. In some examples, the processes described herein can be performed by the image capture and processing system 100, the image capture device 105A, the image processing device 105B, the image processor 150, the ISP 154, the host processor 152, the imaging system 200, the server(s) 205, the user device 210, the user device 220, the HMD 310, the mobile handset 410, the imaging system of FIG. 5, neural network 600, the computing system 800, the processor 810, or a combination thereof The computing device can include any suitable device, such as a mobile device (e.g., a mobile phone), a desktop computing device, a tablet computing device, a wearable device (e.g., a VR headset, an AR headset, AR glasses, a network-connected watch or smartwatch, or other wearable device), a server computer, an autonomous vehicle or computing device of an autonomous vehicle, a robotic device, a television, and/or any other computing device with the resource capabilities to perform the processes described herein. In some cases, the computing device or apparatus may include various components, such as one or more input devices, one or more output devices, one or more processors, one or more microprocessors, one or more microcomputers, one or more cameras, one or more sensors, and/or other component(s) that are configured to carry out the steps of processes described herein. In some examples, the computing device may include a display, a network interface configured to communicate and/or receive the data, any combination thereof, and/or other component(s). The network interface may be configured to communicate and/or receive Internet Protocol (IP) based data or other type of data.

The components of the computing device can be implemented in circuitry. For example, the components can include and/or can be implemented using electronic circuits or other electronic hardware, which can include one or more programmable electronic circuits (e.g., microprocessors, graphics processing units (GPUs), digital signal processors (DSPs), central processing units (CPUs), and/or other suitable electronic circuits), and/or can include and/or be implemented using computer software, firmware, or any combination thereof, to perform the various operations described herein.

The processes described herein are illustrated as logical flow diagrams, block diagrams, or conceptual diagrams, the operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Additionally, the processes described herein may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable or machine-readable storage medium, for example, in the form of a computer program comprising a plurality of instructions executable by one or more processors. The computer-readable or machine-readable storage medium may be non-transitory.

Figure 8:
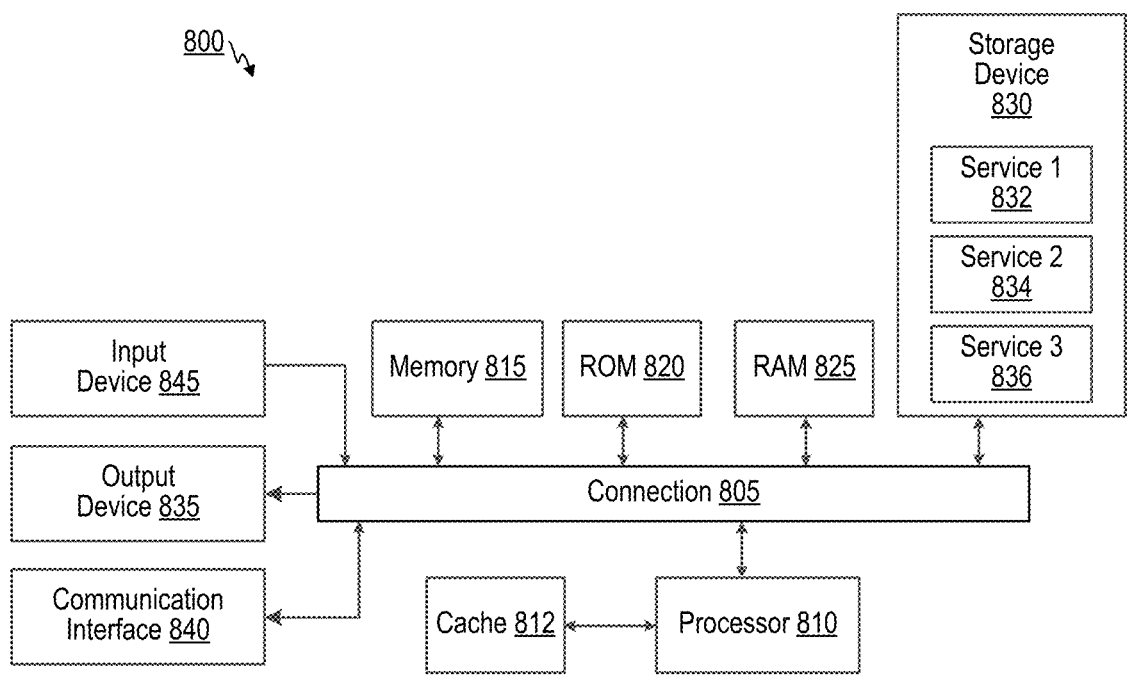
FIG. 8 is a diagram illustrating an example of a computing system for implementing certain aspects described herein.

FIG. 8 is a diagram illustrating an example of a system for implementing certain aspects of the present technology. In particular, FIG. 8 illustrates an example of computing system 800, which can be for example any computing device making up internal computing system, a remote computing system, a camera, or any component thereof in which the components of the system are in communication with each other using connection 805. Connection 805 can be a physical connection using a bus, or a direct connection into processor 810, such as in a chipset architecture. Connection 805 can also be a virtual connection, networked connection, or logical connection.

In some aspects, computing system 800 is a distributed system in which the functions described in this disclosure can be distributed within a datacenter, multiple data centers, a peer network, etc. In some aspects, one or more of the described system components represents many such components each performing some or all of the function for which the component is described. In some aspects, the components can be physical or virtual devices.

Example system 800 includes at least one processing unit (CPU or processor) 810 and connection 805 that couples various system components including system memory 815, such as read-only memory (ROM) 820 and random access memory (RAM) 825 to processor 810. Computing system 800 can include a cache 812 of high-speed memory connected directly with, in close proximity to, or integrated as part of processor 810.

Processor 810 can include any general purpose processor and a hardware service or software service, such as services 832, 834, and 836 stored in storage device 830, configured to control processor 810 as well as a special-purpose processor where software instructions are incorporated into the actual processor design. Processor 810 may essentially be a completely self-contained computing system, containing multiple cores or processors, a bus, memory controller, cache, etc. A multi-core processor may be symmetric or asymmetric.

To enable user interaction, computing system 800 includes an input device 845, which can represent any number of input mechanisms, such as a microphone for speech, a touch-sensitive screen for gesture or graphical input, keyboard, mouse, motion input, speech, etc. Computing system 800 can also include output device 835, which can be one or more of a number of output mechanisms. In some instances, multimodal systems can enable a user to provide multiple types of input/output to communicate with computing system 800. Computing system 800 can include communications interface 840, which can generally govern and manage the user input and system output. The communication interface may perform or facilitate receipt and/or transmission wired or wireless communications using wired and/or wireless transceivers, including those making use of an audio jack/plug, a microphone jack/plug, a universal serial bus (USB) port/plug, an Apple® Lightning® port/plug, an Ethernet port/plug, a fiber optic port/plug, a proprietary wired port/plug, a BLUETOOTH® wireless signal transfer, a BLUETOOTH® low energy (BLE) wireless signal transfer, an IBEACON® wireless signal transfer, a radio-frequency identification (RFID) wireless signal transfer, near-field communications (NFC) wireless signal transfer, dedicated short range communication (DSRC) wireless signal transfer, 802.11 Wi-Fi wireless signal transfer, wireless local area network (WLAN) signal transfer, Visible Light Communication (VLC), Worldwide Interoperability for Microwave Access (WiMAX), Infrared (IR) communication wireless signal transfer, Public Switched Telephone Network (PSTN) signal transfer, Integrated Services Digital Network (ISDN) signal transfer, 3 G/4 G/5 G/LTE cellular data network wireless signal transfer, ad-hoc network signal transfer, radio wave signal transfer, microwave signal transfer, infrared signal transfer, visible light signal transfer, ultraviolet light signal transfer, wireless signal transfer along the electromagnetic spectrum, or some combination thereof. The communications interface 840 may also include one or more Global Navigation Satellite System (GNSS) receivers or transceivers that are used to determine a location of the computing system 800 based on receipt of one or more signals from one or more satellites associated with one or more GNSS systems. GNSS systems include, but are not limited to, the US-based Global Positioning System (GPS), the Russia-based Global Navigation Satellite System (GLONASS), the China-based BeiDou Navigation Satellite System (BDS), and the Europe-based Galileo GNSS. There is no restriction on operating on any particular hardware arrangement, and therefore the basic features here may easily be substituted for improved hardware or firmware arrangements as they are developed.

Storage device 830 can be a non-volatile and/or non-transitory and/or computer-readable memory device and can be a hard disk or other types of computer readable media which can store data that are accessible by a computer, such as magnetic cassettes, flash memory cards, solid state memory devices, digital versatile disks, cartridges, a floppy disk, a flexible disk, a hard disk, magnetic tape, a magnetic strip/stripe, any other magnetic storage medium, flash memory, memristor memory, any other solid-state memory, a compact disc read only memory (CD-ROM) optical disc, a rewritable compact disc (CD) optical disc, digital video disk (DVD) optical disc, a blu-ray disc (BDD) optical disc, a holographic optical disk, another optical medium, a secure digital (SD) card, a micro secure digital (microSD) card, a Memory Stick® card, a smartcard chip, a EMV chip, a subscriber identity module (SIM) card, a mini/micro/nano/pico SIM card, another integrated circuit (IC) chip/card, random access memory (RAM), static RAM (SRAM), dynamic RAM (DRAM), read-only memory (ROM), programmable read-only memory (PROM), erasable programmable read-only memory (EPROM), electrically erasable programmable read-only memory (EEPROM), flash EPROM (FLASHEPROM), cache memory (L1/L2/L3/L4/L5/L#), resistive random-access memory (RRAM/ReRAM), phase change memory (PCM), spin transfer torque RAM (STT-RAM), another memory chip or cartridge, and/or a combination thereof The storage device 830 can include software services, servers, services, etc., that when the code that defines such software is executed by the processor 810, it causes the system to perform a function. In some aspects, a hardware service that performs a particular function can include the software component stored in a computer-readable medium in connection with the necessary hardware components, such as processor 810, connection 805, output device 835, etc., to carry out the function.

As used herein, the term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted using any suitable means including memory sharing, message passing, token passing, network transmission, or the like.

In some aspects, the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Specific details are provided in the description above to provide a thorough understanding of the aspects and examples provided herein. However, it will be understood by one of ordinary skill in the art that the aspects may be practiced without these specific details. For clarity of explanation, in some instances the present technology may be presented as including individual functional blocks including functional blocks comprising devices, device components, steps or routines in a method embodied in software, or combinations of hardware and software. Additional components may be used other than those shown in the figures and/or described herein. For example, circuits, systems, networks, processes, and other components may be shown as components in block diagram form in order not to obscure the aspects in unnecessary detail. In other instances, well-known circuits, processes, algorithms, structures, and techniques may be shown without unnecessary detail in order to avoid obscuring the aspects.

Individual aspects may be described above as a process or method which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

Processes and methods according to the above-described examples can be implemented using computer-executable instructions that are stored or otherwise available from computer-readable media. Such instructions can include, for example, instructions and data which cause or otherwise configure a general purpose computer, special purpose computer, or a processing device to perform a certain function or group of functions. Portions of computer resources used can be accessible over a network. The computer executable instructions may be, for example, binaries, intermediate format instructions such as assembly language, firmware, source code, etc. Examples of computer-readable media that may be used to store instructions, information used, and/or information created during methods according to described examples include magnetic or optical disks, flash memory, USB devices provided with non-volatile memory, networked storage devices, and so on.

Devices implementing processes and methods according to these disclosures can include hardware, software, firmware, middleware, microcode, hardware description languages, or any combination thereof, and can take any of a variety of form factors. When implemented in software, firmware, middleware, or microcode, the program code or code segments to perform the necessary tasks (e.g., a computer-program product) may be stored in a computer-readable or machine-readable medium. A processor(s) may perform the necessary tasks. Typical examples of form factors include laptops, smart phones, mobile phones, tablet devices or other small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are example means for providing the functions described in the disclosure.

In the foregoing description, aspects of the application are described with reference to specific aspects thereof, but those skilled in the art will recognize that the application is not limited thereto. Thus, while illustrative aspects of the application have been described in detail herein, it is to be understood that the inventive concepts may be otherwise variously embodied and employed, and that the appended claims are intended to be construed to include such variations, except as limited by the prior art. Various features and aspects of the above-described application may be used individually or jointly. Further, aspects can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate aspects, the methods may be performed in a different order than that described.

One of ordinary skill will appreciate that the less than ("<") and greater than (">") symbols or terminology used herein can be replaced with less than or equal to ("≤") and greater than or equal to ("≥") symbols, respectively, without departing from the scope of this description.

Where components are described as being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

The phrase "coupled to" refers to any component that is physically connected to another component either directly or indirectly, and/or any component that is in communication with another component (e.g., connected to the other component over a wired or wireless connection, and/or other suitable communication interface) either directly or indirectly.

Claim language or other language reciting "at least one of" a set and/or "one or more" of a set indicates that one member of the set or multiple members of the set (in any combination) satisfy the claim. For example, claim language reciting "at least one of A and B" means A, B, or A and B. In another example, claim language reciting "at least one of A, B, and C" means A, B, C, or A and B, or A and C, or B and C, or A and B and C. The language "at least one of" a set and/or "one or more" of a set does not limit the set to the items listed in the set. For example, claim language reciting "at least one of A and B" can mean A, B, or A and B, and can additionally include items not listed in the set of A and B.

The various illustrative logical blocks, modules, circuits, and algorithm steps described in connection with the aspects disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present application.

The techniques described herein may also be implemented in electronic hardware, computer software, firmware, or any combination thereof. Such techniques may be implemented in any of a variety of devices such as general purposes computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding, or incorporated in a combined video encoder-decoder (CODEC).

Illustrative aspects of the disclosure include:

Aspect 1: An apparatus for media processing, the apparatus comprising: a memory; and one or more processors coupled to the memory, the one or more processors configured to: receive image data representing at least a portion of a first user as captured by a first image sensor; identify that a gaze of the first user as represented in the image data is directed toward a displayed representation of at least a portion of a second user; identify an arrangement of representations of users for output; generate modified image data based on the gaze and the arrangement at least in part by modifying the image data to modify at least the portion of the first user in the image data to be visually directed toward a direction corresponding to the second user based on the gaze and the arrangement; and output the modified image data arranged according to the arrangement.

Aspect 2. The apparatus of Aspect 1, wherein, to modify at least the portion of the first user in the image data to be visually directed toward the direction corresponding to the second user, the one or more processors are configured to modify an eye pose of at least one eye of the first user in the image data to be visually directed toward the direction corresponding to the second user.

Aspect 3. The apparatus of any of Aspects 1 to 2, wherein, to modify at least the portion of the first user in the image data to be visually directed toward the direction corresponding to the second user, the one or more processors are configured to modify a head pose of at least part of a head of the first user in the image data to be visually directed toward the direction corresponding to the second user.

Aspect 4. The apparatus of any of Aspects 1 to 3, wherein, to modify at least the portion of the first user in the image data to be visually directed toward the direction corresponding to the second user, the one or more processors are configured to modify a body pose of at least part of a body of the first user in the image data to be visually directed toward the direction corresponding to the second user.

Aspect 5. The apparatus of any of Aspects 1 to 4, wherein the arrangement of representations of users includes the modified image data and second image data representing at least the portion of the second user, wherein the direction corresponding to the second user is a direction from a position of the modified image data in the arrangement to a position of the second image data in the arrangement, wherein at least a component of the direction corresponding to the second user is parallel to an image plane of the arrangement.

Aspect 6. The apparatus of any of Aspects 1 to 5, wherein the second user is a viewer of the modified image data as output according to the arrangement, wherein the direction corresponding to the second user is a direction toward the viewer, wherein at least a component of the direction corresponding to the second user is perpendicular to an image plane of the arrangement.

Aspect 7. The apparatus of any of Aspects 1 to 6, wherein, to generate the modified image data, the one or more processors use one or more trained machine learning models to generate the modified image data at least in part by providing the image data and the gaze and the arrangement as inputs to the one or more trained machine learning models.

Aspect 8. The apparatus of Aspect 7, wherein the one or more trained machine learning models include a generative adversarial network.

Aspect 9. The apparatus of any of Aspects 1 to 8, wherein the one or more processors are configured to: receive second image data representing at least a portion of the second user as captured by a second image sensor.

Aspect 10. The apparatus of Aspect 9, wherein the one or more processors are configured to: identify that a second gaze of the second user as represented in the second image data is directed toward a second gaze area; generate modified second image data based on the second gaze and the arrangement at least in part by modifying the second image data to modify at least the portion of the second user in the second image data to be visually directed toward a direction corresponding to the second gaze area based on the second gaze and the arrangement; and output the modified second image data arranged according to the arrangement.

Aspect 11. The apparatus of Aspect 10, wherein, to generate the modified second image data, the one or more processors use one or more trained machine learning models to generate the modified second image data at least in part by providing the second image data and the second gaze and the arrangement as inputs to the one or more trained machine learning models.

Aspect 12. The apparatus of any of Aspects 10 to 11, wherein the second gaze area includes a displayed representation of at least the portion of the first user, wherein the direction corresponding to the second gaze area is a direction from a position of the modified second image data in the arrangement to a position of the modified image data in the arrangement, wherein at least a component of the direction corresponding to the second gaze area is parallel to an image plane of the arrangement.

Aspect 13. The apparatus of any of Aspects 10 to 12, wherein the second gaze area includes a displayed representation of at least a portion of a third user, wherein the direction corresponding to the second gaze area is a direction from a position of the modified second image data in the arrangement to a position of third image data representing the third user in the arrangement, wherein at least a component of the direction corresponding to the second gaze area is parallel to an image plane of the arrangement.

Aspect 14. The apparatus of any of Aspects 1 to 13, wherein, to generate the modified image data, the one or more processors are configured to: generate intermediate image data at least in part by modifying the image data to modify at least the portion of the first user in the image data to be visually directed toward a forward direction perpendicular to an image plane of the intermediate image data, and generate the modified image data at least in part by modifying the intermediate image data to modify at least the portion of the first user in the intermediate image data to be visually directed toward the direction corresponding to the second user.

Aspect 15. The apparatus of any of Aspects 1 to 14, wherein, to identify that the gaze of the first user as represented in the image data is directed toward the displayed representation of at least the portion of the second user, the one or more processors are configured to analyze the image data in comparison to a known position of the displayed representation of at least the portion of the second user.

Aspect 16. The apparatus of any of Aspects 1 to 15, wherein the one or more processors are configured to: receive prior image data representing at least the portion of the first user and a second portion of the first user, wherein the prior image data is captured by the first image sensor before capture of the image data by the first image sensor, wherein to generate the modified image data, the one or more processors are configured to incorporate at least some of the prior image data that represents the second portion of the first user into the modified image data.

Aspect 17. The apparatus of any of Aspects 1 to 16, wherein, to generate the modified image data, the one or more processors are configured to modify the image data to modify at least the portion of the first user from a realistic form into an avatar form.

Aspect 18. The apparatus of Aspect 17, wherein the first user has a facial expression as represented in the image data, and wherein, to generate the modified image data, the one or more processors are configured to modify the avatar form to apply an indicator of the facial expression to the avatar form.

Aspect 19. The apparatus of any of Aspects 1 to 18, wherein the first user has a facial expression as represented in the image data, and wherein, to generate the modified image data, the one or more processors are configured to modify the image data to modify at least the portion of the first user to mask the facial expression.

Aspect 20. The apparatus of any of Aspects 1 to 19, further comprising: a display, wherein, to output the modified image data arranged according to the arrangement, the one or more processors are configured to display the modified image data using the display.

Aspect 21. The apparatus of any of Aspects 1 to 20, further comprising: a communication interface, wherein, to output the modified image data arranged according to the arrangement, the one or more processors are configured to send the modified image data to a recipient device using the communication interface, wherein the recipient device renders the modified image data arranged according to the arrangement.

Aspect 22. A method for imaging, the method comprising: receiving image data representing at least a portion of a first user as captured by a first image sensor; identifying that a gaze of the first user as represented in the image data is directed toward a displayed representation of at least a portion of a second user; identifying an arrangement of representations of users for output; generating modified image data based on the gaze and the arrangement at least in part by modifying the image data to modify at least the portion of the first user in the image data to be visually directed toward a direction corresponding to the second user based on the gaze and the arrangement; and outputting the modified image data arranged according to the arrangement.

Aspect 23. The method of Aspect 22, wherein modifying at least the portion of the first user in the image data to be visually directed toward the direction corresponding to the second user includes modifying an eye pose of at least one eye of the first user in the image data to be visually directed toward the direction corresponding to the second user.

Aspect 24. The method of any of Aspects 22 to 23, wherein modifying at least the portion of the first user in the image data to be visually directed toward the direction corresponding to the second user includes modifying a head pose of at least part of a head of the first user in the image data to be visually directed toward the direction corresponding to the second user.

Aspect 25. The method of any of Aspects 22 to 24, wherein modifying at least the portion of the first user in the image data to be visually directed toward the direction corresponding to the second user includes modifying a body pose of at least part of a body of the first user in the image data to be visually directed toward the direction corresponding to the second user.

Aspect 26. The method of any of Aspects 22 to 25, wherein the arrangement of representations of users includes the modified image data and second image data representing at least the portion of the second user, wherein the direction corresponding to the second user is a direction from a position of the modified image data in the arrangement to a position of the second image data in the arrangement, wherein at least a component of the direction corresponding to the second user is parallel to an image plane of the arrangement.

Aspect 27. The method of any of Aspects 22 to 26, wherein the second user is a viewer of the modified image data as output according to the arrangement, wherein the direction corresponding to the second user is a direction toward the viewer, wherein at least a component of the direction corresponding to the second user is perpendicular to an image plane of the arrangement.

Aspect 28. The method of any of Aspects 22 to 27, wherein generating the modified image data includes using one or more trained machine learning models to generate the modified image data at least in part by providing the image data and the gaze and the arrangement as inputs to the one or more trained machine learning models.

Aspect 29. The method of Aspect 28, wherein the one or more trained machine learning models include a generative adversarial network.

Aspect 30. The method of any of Aspects 22 to 29, further comprising: receiving second image data representing at least a portion of the second user as captured by a second image sensor.

Aspect 31. The method of Aspect 30, further comprising: identifying that a second gaze of the second user as represented in the second image data is directed toward a second gaze area; generating modified second image data based on the second gaze and the arrangement at least in part by modifying the second image data to modify at least the portion of the second user in the second image data to be visually directed toward a direction corresponding to the second gaze area based on the second gaze and the arrangement; and outputting the modified second image data arranged according to the arrangement.

Aspect 32. The method of Aspect 31, wherein generating the modified second image data includes using one or more trained machine learning models to generate the modified second image data at least in part by providing the second image data and the second gaze and the arrangement as inputs to the one or more trained machine learning models.

Aspect 33. The method of any of Aspects 31 to 32, wherein the second gaze area includes a displayed representation of at least the portion of the first user, wherein the direction corresponding to the second gaze area is a direction from a position of the modified second image data in the arrangement to a position of the modified image data in the arrangement, wherein at least a component of the direction corresponding to the second gaze area is parallel to an image plane of the arrangement.

Aspect 34. The method of any of Aspects 31 to 33, wherein the second gaze area includes a displayed representation of at least a portion of a third user, wherein the direction corresponding to the second gaze area is a direction from a position of the modified second image data in the arrangement to a position of third image data representing the third user in the arrangement, wherein at least a component of the direction corresponding to the second gaze area is parallel to an image plane of the arrangement.

Aspect 35. The method of any of Aspects 22 to 34, wherein generating the modified image data includes: generating intermediate image data at least in part by modifying the image data to modify at least the portion of the first user in the image data to be visually directed toward a forward direction perpendicular to an image plane of the intermediate image data, and generating the modified image data at least in part by modifying the intermediate image data to modify at least the portion of the first user in the intermediate image data to be visually directed toward the direction corresponding to the second user.

Aspect 36. The method of any of Aspects 22 to 35, wherein identifying that the gaze of the first user as represented in the image data is directed toward the displayed representation of at least the portion of the second user includes analyzing the image data in comparison to a known position of the displayed representation of at least the portion of the second user.

Aspect 37. The method of any of Aspects 22 to 36, further comprising: receiving prior image data representing at least the portion of the first user and a second portion of the first user, wherein the prior image data is captured by the first image sensor before capture of the image data by the first image sensor, wherein generating the modified image data includes incorporating at least some of the prior image data that represents the second portion of the first user into the modified image data.

Aspect 38. The method of any of Aspects 22 to 37, wherein generating the modified image data includes modifying the image data to modify at least the portion of the first user from a realistic form into an avatar form.

Aspect 39. The method of Aspect 38, wherein the first user has a facial expression as represented in the image data, and wherein generating the modified image data includes modifying the avatar form to apply an indicator of the facial expression to the avatar form.

Aspect 40. The method of any of Aspects 22 to 39, wherein the first user has a facial expression as represented in the image data, and wherein generating the modified image data includes modifying the image data to modify at least the portion of the first user to mask the facial expression.

Aspect 41. The method of any of Aspects 22 to 40, wherein outputting the modified image data arranged according to the arrangement includes displaying the modified image data using a display.

Aspect 42. The method of any of Aspects 22 to 41, wherein outputting the modified image data arranged according to the arrangement includes sending the modified image data to a recipient device using a communication interface, wherein the recipient device renders the modified image data arranged according to the arrangement.

Aspect 43: A non-transitory computer-readable medium having stored thereon instructions that, when executed by one or more processors, cause the one or more processors to: receive image data representing at least a portion of a first user as captured by a first image sensor; identify that a gaze of the first user as represented in the image data is directed toward a displayed representation of at least a portion of a second user; identify an arrangement of representations of users for output; generate modified image data based on the gaze and the arrangement at least in part by modifying the image data to modify at least the portion of the first user in the image data to be visually directed toward a direction corresponding to the second user based on the gaze and the arrangement; and output the modified image data arranged according to the arrangement.

Aspect 44: The non-transitory computer-readable medium of Aspect 43, further comprising operations according to any of Aspects 2 to 21, and/or any of Aspects 22 to 42.

Aspect 45: An apparatus for image processing, the apparatus comprising: means for receiving image data representing at least a portion of a first user as captured by a first image sensor; means for identifying that a gaze of the first user as represented in the image data is directed toward a displayed representation of at least a portion of a second user; means for identifying an arrangement of representations of users for output; means for generating modified image data based on the gaze and the arrangement at least in part by modifying the image data to modify at least the portion of the first user in the image data to be visually directed toward a direction corresponding to the second user based on the gaze and the arrangement; and means for outputting the modified image data arranged according to the arrangement.

Aspect 46: The apparatus of Aspect 45, further comprising means for performing operations according to any of Aspects 2 to 21, and/or any of Aspects 22 to 42.

What is claimed is:

1. An apparatus for imaging, the apparatus comprising:
at least one memory; and
one or more processors coupled to the at least one memory, the one or more processors configured to:
receive image data representing at least a portion of a first user as captured by a first image sensor;
identify that a gaze of the first user as represented in the image data is directed toward a displayed representation of at least a portion of a second user;
identify an arrangement of representations of users for output;
generate modified image data based on the gaze and the arrangement at least in part by modifying the image data to modify at least the portion of the first user in the image data to be visually directed toward a direction corresponding to the second user based on the gaze and the arrangement; and
output the modified image data arranged according to the arrangement.

2. The apparatus of claim 1, wherein, to modify at least the portion of the first user in the image data to be visually directed toward the direction corresponding to the second user, the one or more processors are configured to modify an eye pose of at least one eye of the first user in the image data to be visually directed toward the direction corresponding to the second user.

3. The apparatus of claim 1, wherein, to modify at least the portion of the first user in the image data to be visually directed toward the direction corresponding to the second user, the one or more processors are configured to modify a head pose of at least part of a head of the first user in the image data to be visually directed toward the direction corresponding to the second user.

4. The apparatus of claim 1, wherein, to modify at least the portion of the first user in the image data to be visually directed toward the direction corresponding to the second user, the one or more processors are configured to modify a body pose of at least part of a body of the first user in the image data to be visually directed toward the direction corresponding to the second user.

5. The apparatus of claim 1, wherein the arrangement of representations of users includes the modified image data and second image data representing at least the portion of the second user, wherein the direction corresponding to the second user is a direction from a position of the modified image data in the arrangement to a position of the second image data in the arrangement, wherein at least a component of the direction corresponding to the second user is parallel to an image plane of the arrangement.

6. The apparatus of claim 1, wherein the second user is a viewer of the modified image data as output according to the arrangement, wherein the direction corresponding to the second user is a direction toward the viewer, wherein at least a component of the direction corresponding to the second user is perpendicular to an image plane of the arrangement.

7. The apparatus of claim 1, wherein, to generate the modified image data, the one or more processors use one or more trained machine learning models to generate the modified image data at least in part by providing the image data and the gaze and the arrangement as inputs to the one or more trained machine learning models.

8. The apparatus of claim 7, wherein the one or more trained machine learning models include a generative adversarial network.

9. The apparatus of claim 1, wherein the one or more processors are configured to:
receive second image data representing at least a portion of the second user as captured by a second image sensor.

10. The apparatus of claim 9, wherein the one or more processors are configured to:
identify that a second gaze of the second user as represented in the second image data is directed toward a second gaze area;
generate modified second image data based on the second gaze and the arrangement at least in part by modifying the second image data to modify at least the portion of the second user in the second image data to be visually directed toward a direction corresponding to the second gaze area based on the second gaze and the arrangement; and
output the modified second image data arranged according to the arrangement.

11. The apparatus of claim 10, wherein, to generate the modified second image data, the one or more processors use one or more trained machine learning models to generate the modified second image data at least in part by providing the second image data and the second gaze and the arrangement as inputs to the one or more trained machine learning models.

12. The apparatus of claim 10, wherein the second gaze area includes a displayed representation of at least the portion of the first user, wherein the direction corresponding to the second gaze area is a direction from a position of the modified second image data in the arrangement to a position of the modified image data in the arrangement, wherein at least a component of the direction corresponding to the second gaze area is parallel to an image plane of the arrangement.

13. The apparatus of claim 10, wherein the second gaze area includes a displayed representation of at least a portion of a third user, wherein the direction corresponding to the second gaze area is a direction from a position of the modified second image data in the arrangement to a position of third image data representing the third user in the arrangement, wherein at least a component of the direction corresponding to the second gaze area is parallel to an image plane of the arrangement.

14. The apparatus of claim 1, wherein, to generate the modified image data, the one or more processors are configured to:
generate intermediate image data at least in part by modifying the image data to modify at least the portion of the first user in the image data to be visually directed toward a forward direction perpendicular to an image plane of the intermediate image data, and
generate the modified image data at least in part by modifying the intermediate image data to modify at least the portion of the first user in the intermediate image data to be visually directed toward the direction corresponding to the second user.

15. The apparatus of claim 1, wherein, to identify that the gaze of the first user as represented in the image data is directed toward the displayed representation of at least the portion of the second user, the one or more processors are configured to analyze the image data in comparison to a known position of the displayed representation of at least the portion of the second user.

16. The apparatus of claim 1, wherein the one or more processors are configured to:
receive prior image data representing at least the portion of the first user and a second portion of the first user, wherein the prior image data is captured by the first image sensor before capture of the image data by the first image sensor, wherein to generate the modified image data, the one or more processors are configured to incorporate at least some of the prior image data that represents the second portion of the first user into the modified image data.

17. The apparatus of claim 1, wherein, to generate the modified image data, the one or more processors are configured to modify the image data to modify at least the portion of the first user from a realistic form into an avatar form.

18. The apparatus of claim 17, wherein the first user has a facial expression as represented in the image data, and wherein, to generate the modified image data, the one or more processors are configured to modify the avatar form to apply an indicator of the facial expression to the avatar form.

19. The apparatus of claim 1, wherein the first user has a facial expression as represented in the image data, and wherein, to generate the modified image data, the one or more processors are configured to modify the image data to modify at least the portion of the first user to mask the facial expression.

20. The apparatus of claim 1, further comprising:
a display, wherein, to output the modified image data arranged according to the arrangement, the one or more processors are configured to display the modified image data using the display.

21. The apparatus of claim 1, further comprising:
a communication interface, wherein, to output the modified image data arranged according to the arrangement, the one or more processors are configured to send the modified image data to a recipient device using the communication interface, wherein the recipient device renders the modified image data arranged according to the arrangement.

22. A method for imaging, the method comprising:
receiving image data representing at least a portion of a first user as captured by a first image sensor;
identifying that a gaze of the first user as represented in the image data is directed toward a displayed representation of at least a portion of a second user;
identifying an arrangement of representations of users for output;
generating modified image data based on the gaze and the arrangement at least in part by modifying the image data to modify at least the portion of the first user in the image data to be visually directed toward a direction corresponding to the second user based on the gaze and the arrangement; and
outputting the modified image data arranged according to the arrangement.

23. The method of claim 22, wherein modifying at least the portion of the first user in the image data to be visually directed toward the direction corresponding to the second user includes at least one of modifying an eye pose of at least one eye of the first user in the image data to be visually directed toward the direction corresponding to the second user, modifying a head pose of at least part of a head of the first user in the image data to be visually directed toward the direction corresponding to the second user, or modifying a body pose of at least part of a body of the first user in the image data to be visually directed toward the direction corresponding to the second user.

24. The method of claim 22, wherein the arrangement of representations of users includes the modified image data and second image data representing at least the portion of the second user, wherein the direction corresponding to the second user is a direction from a position of the modified image data in the arrangement to a position of the second image data in the arrangement, wherein at least a component of the direction corresponding to the second user is parallel to an image plane of the arrangement.

25. The method of claim 22, wherein the second user is a viewer of the modified image data as output according to the arrangement, wherein the direction corresponding to the second user is a direction toward the viewer, wherein at least a component of the direction corresponding to the second user is perpendicular to an image plane of the arrangement.

26. The method of claim 22, wherein generating the modified image data includes using one or more trained machine learning models to generate the modified image data at least in part by providing the image data and the gaze and the arrangement as inputs to the one or more trained machine learning models.

27. The method of claim 22, further comprising:
receiving second image data representing at least a portion of the second user as captured by a second image sensor;
identifying that a second gaze of the second user as represented in the second image data is directed toward a second gaze area;
generating modified second image data based on the second gaze and the arrangement at least in part by modifying the second image data to modify at least the portion of the second user in the second image data to be visually directed toward a direction corresponding to the second gaze area based on the second gaze and the arrangement; and
outputting the modified second image data arranged according to the arrangement.

28. The method of claim 22, wherein generating the modified image data includes:
generating intermediate image data at least in part by modifying the image data to modify at least the portion of the first user in the image data to be visually directed toward a forward direction perpendicular to an image plane of the intermediate image data, and
generating the modified image data at least in part by modifying the intermediate image data to modify at least the portion of the first user in the intermediate image data to be visually directed toward the direction corresponding to the second user.

29. The method of claim 22, wherein identifying that the gaze of the first user as represented in the image data is directed toward the displayed representation of at least the portion of the second user includes analyzing the image data in comparison to a known position of the displayed representation of at least the portion of the second user.

30. The method of claim 22, wherein outputting the modified image data arranged according to the arrangement includes sending the modified image data to a recipient device using a communication interface, wherein the recipient device renders the modified image data arranged according to the arrangement.

* * * * *